US009758564B2

(12) United States Patent
Lee et al.

(10) Patent No.: US 9,758,564 B2
(45) Date of Patent: Sep. 12, 2017

(54) ACID-RESISTANT YEAST CELL WITH REDUCED FPS1 ACTIVITY AND METHOD OF PRODUCING LACTATE BY USING THE YEAST CELL

(71) Applicant: Samsung Electronics Co., Ltd., Suwon-si, Gyeonggi-do (KR)

(72) Inventors: Juyoung Lee, Daegu (KR); Hyunyoung Shin, Suwon-si (KR); Changduk Kang, Gwacheon-si (KR); Seunghyun Lee, Asan-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 62 days.

(21) Appl. No.: 14/747,848

(22) Filed: Jun. 23, 2015

(65) Prior Publication Data

US 2015/0368306 A1 Dec. 24, 2015

(30) Foreign Application Priority Data

Jun. 23, 2014 (KR) .................. 10-2014-0076636

(51) Int. Cl.
*C12N 1/14* (2006.01)
*C07K 14/705* (2006.01)
*C12P 7/56* (2006.01)
*C07K 14/395* (2006.01)

(52) U.S. Cl.
CPC .......... *C07K 14/705* (2013.01); *C07K 14/395* (2013.01); *C12P 7/56* (2013.01); *C12Y 101/01027* (2013.01)

(58) Field of Classification Search
CPC ..................................................... C12P 7/56
USPC ............................................ 435/161, 254.21
See application file for complete search history.

(56) References Cited

U.S. PATENT DOCUMENTS 8,956,851 B2 * 2/2015 Argyros ............... C12N 9/0006
435/161
2011/0250664 A1 10/2011 Ma

FOREIGN PATENT DOCUMENTS

| JP | 2001-204468 A | 7/2001 |
| JP | 2006-075133 A | 3/2006 |
| KR | 2011/0116438 A | 10/2011 |

OTHER PUBLICATIONS

Colombie et al. (2003) Control of lactate production by *Saccharomyces cerevisiae* expressing a bacterial LDH gene, Enzyme and Microbial Technology (2003), 33(1), 38-46.*
Lee et al., "MAPK Hog1 closes the *S. cerevisiae* glycerol channel Fps1 by phosphorylating and displacing its positive regulators", *Genes & Development*, 27: 2590-2601 (2013).
Lourenco et al., "Quantitative 1H-NMR-Metabolomics Reveals Extensive Metabolic Reprogramming and the Effect of the Aquaglyceroporin FPS1 in Ethanol-Stressed Yeast Cells", PLOS One, 8(2): 1-12 (2013).
Shepherd et al., "The Fps1p aquaglyceroporin facilitates the use of small aliphatic amides as a nitrogen source by amidase-expressing yeasts", *FEMS Yeast Res*, 10, pp. 527-534 (2010).

* cited by examiner

*Primary Examiner* — Tekchand Saidha
(74) *Attorney, Agent, or Firm* — Leydig, Voit & Mayer, Ltd.

(57) ABSTRACT

Provided are an acid-resistant yeast cell with genetic modification and reduced Fps1 activity compared to that of a parent cell without the genetic modification; and a method of producing lactate by using the yeast cell.

20 Claims, 7 Drawing Sheets

ACID-RESISTANT YEAST CELL WITH REDUCED FPS1 ACTIVITY AND METHOD OF PRODUCING LACTATE BY USING THE YEAST CELL

RELATED APPLICATION

This application claims the benefit of Korean Patent Application No. 10-2014-0076636, filed on Jun. 23, 2014, in the Korean Intellectual Property Office, the disclosure of which is incorporated herein in its entirety by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 65,020 byte ASCII (Text) file named "720021.ST25.TXT," created Jun. 17, 2015.

BACKGROUND

1. Field

The present disclosure relates to an acid-resistant yeast cell with reduced Fps1 activity and a method of producing lactate by using the yeast cell.

2. Description of the Related Art

Organic acids are widely used in a variety of industries. For example, lactate is an organic acid that is used in a variety of industrial fields, including food, pharmaceutical, chemical, and electronic industries. Lactate is a colorless, odorless, water-soluble, low-volatile material. Lactate is also not toxic to the human body, and is used as a flavoring agent, a sour taste agent, a preserving agent, or the like. Lactate is also used as a source of polylactic acid (PLA) that is an environmentally friendly, biodegradable plastic known as an alternate polymeric material.

Organic acids may be dissociated into hydrogen ions and their own negative ions at a higher pH than their own dissociation constant (pKa value), for example, under a neutral condition. Meanwhile, organic acids, for example, lactic acid, may be present in the form of free acid without an electromagnetic force at a pH lower than its own pKa value. An organic acid in the form of negative ions may not be permeable with respect to a cell membrane, but may be permeable with respect to the cell membrane when it is present in the form of free acid. Therefore, an organic acid in free acid form may flow into the cells from extracellular environments where the concentration of the organic acid is high, and thus lower an intercellular pH level. Meanwhile, an organic acid present as negative ions requires an additional isolation process involving the addition of a salt. Thus, a cell lacking acid-resistance may become inactive and die under acidic conditions, such as cells exposed to lactic acid during a lactate production process.

Therefore, there is a need for a microorganism with acid-resistance used in the production of lactate.

SUMMARY

Provided is an acid-resistant yeast cell comprising a genetic modification that reduces Fps1 activity in the acid-resistant yeast cell compared to a parent cell without the genetic modification.

Also provided is a method of producing lactate by culturing the yeast cell in a cell culture medium.

Further provided is a method of increasing the acid-resistance of a yeast cell, the method comprising deleting or disrupting expression of a polynucleotide that encodes the Fps1 in a yeast cell to increase the acid-resistance of the yeast cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
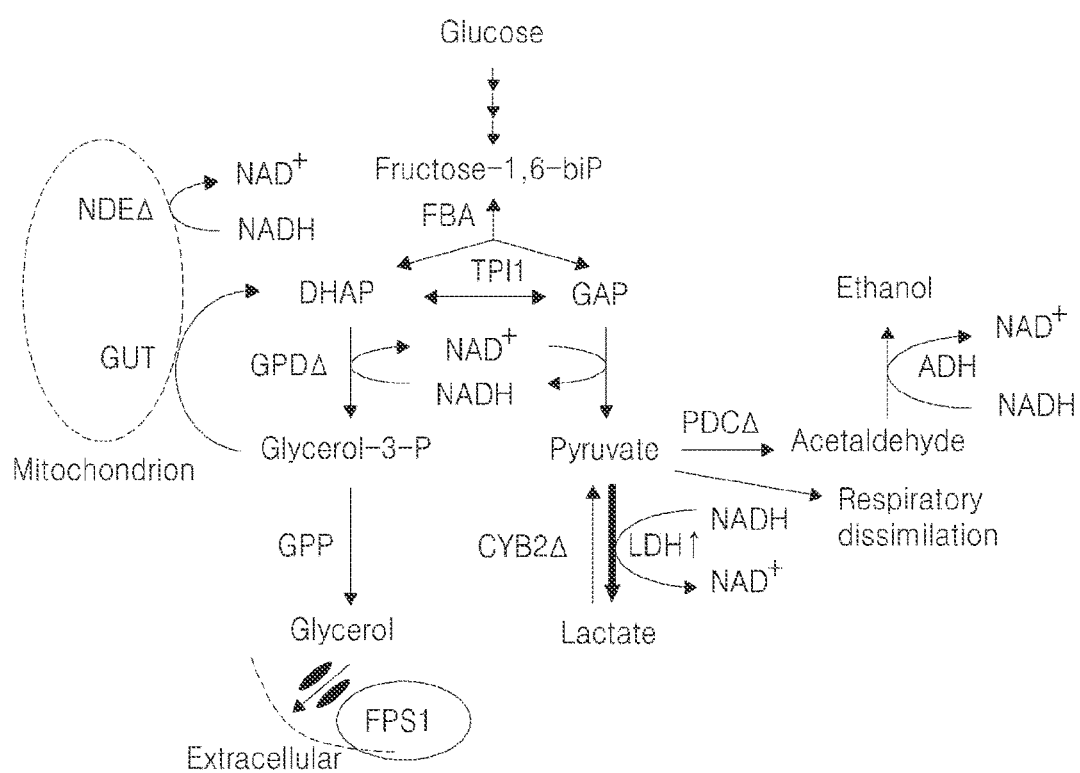
FIG. 1 illustrates a lactate production pathway of an acid-resistant yeast cell according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the term "activity reduction," "reduced activity" and like terms in reference to an enzyme or a polypeptide denotes a cell, an isolated enzyme, or a polypeptide whose activity is lower than the activity measured in a comparable cell of the same type or the original polypeptide. Additionally, activity reduction may refer to a cell, an isolated enzyme, or a polypeptide having no activity. The activity of a subject enzyme or polypeptide of a genetically engineered cell may be reduced by any amount, such as reduced by about 5% or more, about 10% or more, about 15% or more, about 20% or more, about 30% or more, about 40% or more, about 50% or more, about 55% or more, about 60% or more, about 70% or more, about 75% or more, about 80% or more, about 85% or more, about 90% or more, about 95% or more, or about 100% as compared to the activity of an enzyme or polypeptide measured in a comparable cell of the same type that does not have a given genetic modification (e.g. a parent cell or "wild-type" cell). The activity of a specific enzyme or polypeptide in a subject cell may be about 5% or more, about 10% or more, about 15% or more, about 20% or more, about 30% or more, about 50% or more, about 60% or more, about 70% or more, or about 100% or more reduced than the activity of the enzyme or polypeptide in a parent cell. The reduced activity of the enzyme or polypeptide may be confirmed by using a commonly known method in the art.

Activity of the enzyme or polypeptide of the yeast cell may be reduced due to mutation such as deletion or disruption of a gene that encodes the enzyme or polypeptide. As used herein, the "deletion" or "disruption" of the gene includes situations where a part or a whole gene, or a part or a whole regulatory region of a promoter or terminator of the gene is mutated, substituted, deleted, or at least one base is inserted into the gene, such that the gene is not expressed or has a reduced amount of expression, or activity of the enzyme is removed or reduced even when the gene is expressed. The deletion or disruption of the gene may be caused by genetic engineering such as homologous recombination, mutation induction, or molecular evolution. When a cell includes a plurality of the same genes or at least two different polypeptide paralogs, at least one gene may be deleted or disrupted.

As used herein, the term "activity increase" or "increased activity" or like terms used in reference to an enzyme or a polypeptide refers to situations where an amount of an enzyme or a polypeptide is increased enough so as to increase the activity thereof. Additionally, the terms "activity increase" or "increased activity" or like terms denotes a cell or an isolated polypeptide that has been genetically modified such that a specified activity is increased as compared to the same activity measured in a comparable cell of the same type that has not been engineered (e.g., parent cell or "wild-type" cell) or the original polypeptide that has not been genetically engineered. The activity can be increased by any suitable amount. For instance, activity of a subject enzyme or polypeptide in a genetically engineered cell may be increased by about 5% or more, about 10% or more, about 15% or more, about 20% or more, about 30% or more, about 50% or more, about 60% or more, about 70% or more, or about 100% or more as compared to the activity of an enzyme or polypeptide measured in a comparable cell of the same type that does not contain the genetic modification (e.g., parent cell or "wild-type" cell). Also, the activity of a specific enzyme or polypeptide in a subject cell may be increased by about 5% or more, about 10% or more, about 15% or more, about 20% or more, about 30% or more, about 50% or more, about 60% or more, about 70% or more, or about 100% or more compared to the activity of the enzyme or polypeptide in a parent cell. A cell having increased activity of a polypeptide may be confirmed by using any method commonly known in the art.

An increase in the activity of the enzyme or polypeptide may be caused by an increase in expression of the enzyme or polypeptide, or an increase in a specific activity of the enzyme or polypeptide. An increase in specific activity may be due to enzyme engineering caused by mutation or random mutagenesis of specific amino acid of an active domain in the enzyme or polypeptide. An increase in the expression may be caused by introduction of a polynucleotide encoding a polypeptide into a cell, by an increased number of copies of the polynucleotide, or by mutation of a regulatory region of the polynucleotide. The mutation of a regulatory region of the polynucleotide may be caused by mutation of a promoter. The polynucleotide introduced from the outside of the cell or the polynucleotide having the increased number of copies may be an endogenous gene or an exogenous gene. The term "endogenous" may refer to a gene present in a genetic material contained within the microorganism. The term "exogenous" may refer to a gene introduced into a cell from the outside of the cell, and for example, the exogenous gene to be introduced into a host cell may be a homologous or heterologous with respect to the host cell. The term "heterologous" denotes that the gene is a foreign gene and is non-native to the host cell.

As used herein, the term "activity increase" or "increased activity" of an enzyme or a polypeptide includes the introduction of an activity into a cell that was not present prior to the genetic modification, e.g., an activity that is not in the parent cell by genetic modification.

The expression "increased copy number" includes an increase in copy number by introduction of an exogenous gene or by amplification of an endogenous gene, or both. The introduction of an exogenous gene may occur by using a vehicle such as a vector. The introduction may be a transient introduction, in which the gene is not integrated into the genome, or integration into the genome. The introduction may, for example, occur by introducing a vector inserted with a polynucleotide encoding a desired polypeptide into the cell and then replicating the vector in the cell or integrating the polynucleotide into the genome of the cell and then replicating the polynucleotide together with the replication of the genome.

As used herein, the gene modification may be performed by molecular biological methods known in the art (see, e.g., Roslyn M. Bill, Recombinant Protein Production in Yeast: Methods and Protocols (2012); Sambrook et al., Molecular cloning, A laboratory manual: Cold Spring Harbor Laboratory (1989); and R Daniel Gietz et al., Quick and easy yeast transformation using the LiAc/SS carrier DNA/PEG method: Nature protocols (2007)).

As used herein, the term "gene" denotes a polynucleotide that is expressed by at least one of transcription and translation to produce a gene product, including mRNA or other nucleic acid fragment capable of producing a protein, or the protein expressed therefrom. A gene may include a coding region as well as a regulatory sequence of a 5'-non coding sequence and a 3'-non coding sequence in addition to the coding region.

The terms "cell", "strain", or "microorganism" as used herein may be interchangeably used and may include bacteria, yeast, or fungi.

As used herein, the term "sequence identity" of a polypeptide or polynucleotide with respect to another polypeptide or polynucleotide refers to a degree of sameness in an amino acid residue or a base in a specific region of two sequences that are aligned to best match each other for comparison. The sequence identity is a value obtained via optimal alignment and comparison of the two sequences in the specific region for comparison, in which a partial sequence in the specific region for comparison may be added or deleted with respect to a reference sequence. The sequence identity represented in a percentage may be calculated by, for example, comparing two sequences that are aligned to best match each other in the specific region for comparison, determining matched sites with the same amino acid or base in the two sequences to obtain the number of the matched sites, dividing the number of the matched sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTP or BLASTN (NCBI), CLC Main Workbench (CLC bio), or MegAlign™ (DNASTAR Inc).

In identifying a polypeptide or polynucleotide with the same or similar function or activity with respect to various types of species, any various levels of sequence identity may be applied. In some embodiments, the sequence identity may be, for example, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%.

As used herein, the term "parent cell" or "parent strain" refers to a cell or strain used for a subject genetic modification, i.e., the cell or strain prior to introduction of a given genetic modification that provides a modified cell or strain. The parent cell is the same as a subject modified cell with the exception of the genetic modification present in the subject cell, and thus may be a reference cell with respect to the genetic modification. Also, the term "genetic modification" may refer to situations where the constitution or a structure of a genetic material of a cell is artificially changed. The parent cell may not have the subject genetic modification, that is, for example, a genetic modification resulting in reducing Fps1 activity. The parent cell may be a parent yeast cell. Also, the term "wild-type" polypeptide or polynucleotide may be a polypeptide or a polynucleotide without specific genetic modification, and the specific genetic modification may result a genetically engineered polypeptide or polynucleotide. A wild-type polypeptide or polynucleotide may serve as a basis of comparison with a genetically modified polypeptide or polynucleotide.

As used herein, the term "lactate" is interpreted as including its anion form, a salt thereof, a solvate, a polymorph, or a combination thereof in addition to lactic acid itself. The salt may be, for example, an inorganic acid salt, an organic acid salt, or a metal salt. The inorganic acid salt may be a hydrochloride, bromate, phosphate, sulfate, or disulfate. The inorganic acid salt may be formate, acetate, propionate, lactate, oxalate, tartrate, malate, maleate, citrate, fumarate, besylate, camsylate, edisylate, trifluoroacetate, benzoate, gluconate, methansulfonate, glycolate, succinate, 4-toluenesulfonate, galacturonate, embonate, glutamate, or aspartate. The metal salt may be a calcium salt, a sodium salt, a magnesium salt, a strontium salt, or a potassium salt.

According to an aspect of the present invention, provided is an acid-resistant yeast cell that has a genetic modification that reduces Fps1 activity compared to that of a parent cell without the genetic modification.

In the yeast cell, a polynucleotide that encodes Fps1 may be modified, for example, deleted or disrupted. The Fps1 may be aquaglyceroporin. The Fps1 may be referred to as a glycerol channel protein, a glycerol transport polypeptide, a glycerol facilitator channel, or a glycerol uptake/efflux facilitator protein. Glycerol may be secreted to the outside of a cell through the Fps1. The Fps1 may be classified under TCDB 1.A.8.5.1 in the transporter classification system provided by Transport Classification Database (M. Saier; U of CA, San Diego). A Fps1 protein (Fps1p) may have an amino acid sequence having at least 60%, at least 70%, at least 80%, at least 90%, at least 95%, at least 96%, at least 97%, at least 98%, or at least 99% sequence identity with an amino acid sequence of SEQ ID NO: 1. A polynucleotide that encodes the Fps1 protein may have a polynucleotide sequence that encodes an amino acid having at least 95% sequence identity with an amino acid sequence of SEQ ID NO: 1 or may have a polynucleotide sequence of SEQ ID NO: 2.

The term "acid-resistant", "acid-tolerant", "acid tolerating", "acid-resistance", and "acid tolerance" may be used interchangeably.

The yeast cell with an acid-resistant property of may have a better growth rate under an acid condition compared to the growth of the parent cell. The acid condition may be an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell better under a pH condition in a range of about 2.0 to about 7.0 (below pH 7.0), for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which Fps1 activity is not reduced. The growth rate may be measured by counting microorganism colonies or measuring the optical density (OD) of the colonies. The yeast cell may have increased growth rate as measured by OD compared to that of a yeast cell in which Fps1 activity is not reduced.

The yeast cell with an acid-resistant property of may have a higher survival rate under an acid condition compared to that of a parent cell. The acid condition may be an acid condition including an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may have a higher survival rate under a pH condition in a range of about 2.0 to about 7.0 (below pH 7.0), for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which Fps1 activity is not reduced (e.g., a parent cell).

Also, the yeast cell with an acid-resistant property may have higher (greater) metabolization ability under an acid condition compared to that of a parent cell. The metabolization may mean chemical transformations (e.g., enzyme-catalyzed reactions) within the yeast cell. The enzyme-catalyzed reactions may allow the yeast cell to grow, reproduce, and respond to their environment such as acidic conditions. The metabolization ability may be determined by measuring consumption of a nutrient such as hexose (e.g., glucose) or pentose, or production of metabolite such as lactate in the cell. The acid condition may be an acid condition including an organic acid, an inorganic acid, or a combination thereof. The organic acid may be an organic acid having 1 to 20 carbon atoms. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may have higher metabolization ability under a pH condition in a range of about 2.0 to about 7.0 (below pH 7.0), for example, pH in a range of about 2.0 to about 5.0, about 2.0 to about 4.5, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0 compared to that of a yeast cell in which Fps1 activity is not reduced. Here, a degree of "metabolization ability" may be measured by a nutrition uptake rate per cell, for example, a glucose uptake rate per cell. Also, a degree of "metabolization ability" may be measured by a product secretion rate per cell, for example, a carbon dioxide secretion rate per cell.

The yeast cell may belong to *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus. *Saccharomyces* genus may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*.

The yeast cell may produce lactate. The yeast cell may have an activity of a polypeptide that converts pyruvate into lactate. In the yeast cell, the activity of a polypeptide that converts pyruvate into lactate may be increased compared to a parent cell. The yeast cell may have an exogenous gene encoding a polypeptide that converts pyruvate into lactate or a mutant of the gene. The polypeptide that converts pyruvate into lactate may be a lactate dehydrogenase (LDH). The LDH may be an NAD(P)-dependent enzyme. Also, the LDH may be stereo-specific and may produce only L-lactate, only D-lactate, or both L-lactate and D-lactate. The NAD(P)-dependent enzyme may be an enzyme that is classified under EC 1.1.1.27 that is related to production of L-lactate or EC 1.1.1.28 that is related to production of D-lactate.

In the yeast cell having a capability of producing lactate, an activity of LDH may be increased. The yeast cell may include a gene encoding at least one LDH, and the gene may be exogenous. A polynucleotide may be derived from bacteria, yeasts, fungi, mammals or reptiles. The polynucleotide may be a polynucleotide that encodes at least one LDH selected from the group consisting of *Lactobacillus helveticus*, *L. bulgaricus*, *L. johnsonii*, *L. plantarum*, *Pelodiscus sinensis japonicus*, *Ornithorhynchus anatinus*, *Tursiops truncatus*, *Rattus norvegicus*, *Xenopus laevis*, and *Bos Taurus*. An LDH derived from *Pelodiscus sinensis japonicus*, an LDH derived from *Ornithorhynchus anatinus*, an LDH derived from *Tursiops truncatus*, and an LDH derived from *Rattus norvegicus* may each include an amino acid sequence having a sequence identity of about 60% or more, about 70% or more, about 80% or more, about 90% or more, about 95% or more, about 96% or more, about 97% or more, about 98% or more, or about 99% or more with amino acids of SEQ ID NOS: 3, 4, 5, and 6. For example, a polynucleotide encoding the LDH may be a polynucleotide encoding an amino acid sequence with a sequence identity of about 95% or more with an amino acid sequence of SEQ ID NOS: 3, 4, 5, and 6. In some embodiments, a polynucleotide encoding the LDH may have a polynucleotide sequence encoding an amino acid sequence with about 95% or more with an amino acid sequence of SEQ ID NOS: 3, 4, 5, and 6 or a polynucleotide sequence of SEQ ID NO: 7.

A polynucleotide encoding the LDH may be included in a vector. The vector may include a replication origin, a promoter, a LDH-encoding polynucleotide, and/or a terminator. The replication origin may include a yeast autonomous replication sequence (ARS). The yeast ARS may be stabilized by a yeast centrometric sequence (CEN). The promoter may be a constitutive promoter. For example, the promoter may be selected from the group consisting of a cytochrome c (CYC) promoter, a transcription elongation factor (TEF) promoter, a glyceraldehyde-3-phosphate dehydrogenase (GPD) promoter, and an alcohol dehydrogenase (ADH) promoter. The CYC promoter, the TEF promoter, the GPD promoter, and the ADH promoter may each have a nucleotide sequence of SEQ ID NOS: 19, 20, 21, 22, and 23. The terminator may be selected from the group consisting of a terminator of a gene encoding a phosphoglycerate kinase 1 (PGK1), a terminator of a gene encoding a cytochrome c 1 (CYC1), and a terminator of a gene encoding a galactokinase 1 (GAL1). The CYC1 terminator may have a nucleotide sequence of SEQ ID NO: 24. The vector may further include a selection marker. The LDH-encoding polynucleotide may be included in a specific location of a yeast cell genome. The specific location of the yeast cell genome may include a locus of a gene to be deleted and disrupted, such as pyruvate decarboxylase (PDC) and cytochrome-c oxidoreductase 2 (CYB2). When the LDH-encoding polynucleotide functions to produce an active protein in a cell, the polynucleotide is considered as "functional" in a cell.

The yeast cell may include a polynucleotide that encodes one LDH or a polynucleotide that encodes multiple LDH copies, e.g., 2 to 10 copies. The yeast cell may include a polynucleotide that encodes multiple LDH copies into, for example, 1 to 8, 1 to 7, 1 to 6, 1 to 5, 1 to 4, or 1 to 3 copies. When the yeast cell includes the polynucleotide encoding multiple LDHs, each polynucleotide may include copies of the same LDH polynucleotide or copies of polynucleotides encoding at least two different LDHs. The multiple copies of the polynucleotide encoding exogenous LDHs may be included in the same locus or multiple loci in a genome of a host cell, and the promoter or terminator of each copy of the polynucleotide may be identical to or different from each other.

In some embodiments, in the yeast cell, activity of a polypeptide that converts pyruvate into acetaldehyde, a polypeptide that converts lactate into pyruvate, a polypeptide that converts dihydroxyacetone phosphate (DHAP) into glycerol-3-phosphate, an external mitochondrial NADH dehydrogenase, or a combination thereof may be reduced compared to a parent cell.

In the yeast cell, a gene encoding the polypeptide that converts pyruvate into acetaldehyde may be deleted or disrupted. The polypeptide that converts pyruvate into acetaldehyde may be an enzyme that is classified under EC 4.1.1.1. The polypeptide that converts pyruvate to acetaldehyde may be a pyruvate decarboxylase, that is PDC1. The polypeptide that converts pyruvate to acetaldehyde may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 8. The gene encoding the polypeptide that converts pyruvate to acetaldehyde may be a polynucleotide encoding an amino acid sequence with a sequence identity of about 95% or more with respect to an amino acid sequence of SEQ ID NO: 8, or may have a polynucleotide sequence of SEQ ID NO: 9. The gene may be pdc1.

In the yeast cell, a gene encoding the polypeptide that converts lactate into pyruvate may be deleted or disrupted. The polypeptide that converts lactate into pyruvate may be a cytochrome c-dependent enzyme. The polypeptide that converts lactate into pyruvate may be an enzyme that is classified under EC 1.1.2.4 that acts on D-lactate or EC 1.1.2.3 that acts on L-lactate. The polypeptide that converts lactate into pyruvate may be lactate cytochrome c-oxidoreductase, for example, a CYB2 (CAA86721.1), a CYB2A, a CYB2B, or a DLD1. The polypeptide that converts lactate into pyruvate may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 10. The gene encoding the polypeptide that converts lactate into pyruvate may be a polynucleotide sequence encoding an amino acid sequence having a sequence identity of about 95% or more with an amino acid sequence of SEQ ID NO: 10, or may include a polynucleotide sequence of SEQ ID NO: 11.

In the yeast cell, a gene encoding the polypeptide that converts DHAP into glycerol-3-phosphate may be deleted or disrupted. The polypeptide that converts DHAP into glycerol-3-phosphate may be a cytosolic glycerol-3-phosphate dehydrogenase and may be an enzyme that catalyzes reduction of DHAP to glycerol-3-phosphate by using oxidation of NADH to $NAD^+$. The polypeptide may be classified under EC 1.1.1.8. The cytosolic glycerol-3-phosphate dehydrogenase may be GPD1. The cytosolic glycerol-3-phosphate dehydrogenase may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 12. A gene encoding the cytosolic glycerol-3-phosphate dehydrogenase may include a polynucleotide sequence encoding an amino acid sequence having a sequence identity of about 95% or more with an amino acid sequence of SEQ ID NO: 12, or may include a polynucleotide sequence of SEQ ID NO: 13.

In the yeast cell, a gene encoding the external mitochondrial NADH dehydrogenase may be deleted or disrupted. The external mitochondrial NADH dehydrogenase may be an enzyme that is classified under EC. 1.6.5.9 or EC. 1.6.5.3. The external mitochondrial NADH dehydrogenase may be a type II NADH:ubiquinone oxidoreductase. The external mitochondrial NADH dehydrogenase may be located on the outer surface of the inner mitochondrial membrane facing a cytoplasm. The external mitochondrial NADH dehydrogenase may be an enzyme catalyzing oxidation of cytosolic NADH to NAD+. The external mitochondrial NADH dehydrogenase may re-oxidize cytosolic NADH formed by a glycolysis process. The external mitochondrial NADH dehydrogenase may provide cytosolic NADH to a mitochondrial respiratory chain. The external mitochondrial NADH dehydrogenase may be NDE1, NDE2, or a combination thereof. The external mitochondrial NADH dehydrogenase may be distinguished from an internal mitochondrial NADH dehydrogenase NDI1 that is present and functions inside mitochondria. The external mitochondrial NADH dehydrogenase may include an amino acid sequence having a sequence identity of about 60% or more, about 70% or more, about 80% or more, about 90% or more, about 95% or more, about 96% or more, about 97% or more, about 98% or more, or about 99% or more with an amino acid sequence of SEQ ID NO: 14 or 16. For example, NDE1 and NDE2 may each have amino acid sequences of SEQ ID NO: 14 and SEQ ID NO: 16. The gene encoding the external mitochondrial NADH dehydrogenase may be a polynucleotide sequence encoding an amino acid sequence having a sequence identity of about 95% or more with an amino acid sequence of SEQ ID NO: 14 or 16, or may have a polynucleotide sequence of SEQ ID NO: 15 or 17. In some embodiments, NDE1 may include a polynucleotide sequence of SEQ ID NO: 15, and NDE2 may include a polynucleotide sequence of SEQ ID NO: 17.

In the yeast cell, Fps1 activity is reduced, and a gene encoding a polypeptide that converts pyruvate into acetaldehyde, a gene encoding a polypeptide that converts lactate into pyruvate, a gene encoding a polypeptide that converts DHAP into glycerol-3-phosphate, a gene encoding an external mitochondrial NADH dehydrogenase, or a combination thereof are deleted or disrupted, and a gene encoding a polypeptide that converts pyruvate into lactate is included or additionally introduced to a genome of the yeast cell. The yeast cell may be Saccharomyces cerevisiae.

According to another aspect of the present invention, a composition for producing lactate is provided, wherein the composition includes the yeast cell and a cell culture medium.

According to another aspect of the present invention, a method of producing lactate is provided, wherein the method includes culturing the yeast cell in a cell culture medium, whereby the yeast cell produces lactate.

The culturing of the yeast cell may be performed in a suitable medium under suitable culturing conditions known in the art. One of ordinary skill in the art may suitably change a culture medium and culturing conditions according to the microorganism selected. A culturing method may be batch culturing, continuous culturing, or fed-batch culturing. The yeast cell is as defined above.

The culture medium may include various carbon sources, nitrogen sources, and trace elements.

The carbon source may be, for example, carbohydrate such as glucose, sucrose, lactose, fructose, maltose, starch, or cellulose; fat such as soybean oil, sunflower oil, castor oil, or coconut oil; fatty acid such as palmitic acid, stearic acid, or linoleic acid; alcohol such as glycerol or ethanol; organic acid such as acetic acid, and/or a combination thereof. The culturing may be performed by having glucose as the carbon source. The nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium is a supply source of phosphorus and may include, for example, potassium dihydrogen phosphate, dipotassium phosphate, and corresponding sodium-containing salt thereof, and a metal salt such as magnesium sulfate or iron sulfate. Also, amino acid, vitamin, a suitable precursor, or the like may be included in the culture medium. The culture medium or individual component may be added to a culture medium solution in a batch or continuous manner.

Also, pH of the culture medium solution may be adjusted by adding a compound such as ammonium hydroxide, potassium hydroxide, ammonia, phosphoric acid, and sulfuric acid to the culture medium solution by using a suitable method during the culturing process. Also, an antifoaming agent such as fatty acid polyglycol ester may be used during the culturing process to inhibit the generation of bubbles.

The yeast cell may be cultured under an aerobic, microaerobic, or anaerobic condition. In some embodiments, the microaerobic condition may refer to a culturing condition in which oxygen is dissolved in the medium at a lower level of an oxygen concentration than an oxygen concentration in the atmosphere. The lower level of an oxygen concentration may be about 0.1% to about 10%, about 1% to about 9%, about 2% to about 8%, about 3% to about 7%, or about 4% to about 6% of the oxygen concentration in the atmosphere. Also, the microaerobic condition may include maintaining a dissolved oxygen (DO) concentration of the medium in a range of about 0.9 ppm to about 3.6 ppm, for example, about 0.9 ppm to about 2.6 ppm, about 0.9 ppm to about 1.6 ppm, about 1.0 ppm to about 3.6 ppm, about 2.0 ppm to about 3.6 ppm, or about 3.0 ppm to about 3.6 ppm. A temperature for the culturing may be in a range of, for example, about 20° C. to about 45° C. or about 25° C. to about 45° C. A period of time for the culturing may be continued until a desired amount of lactate is obtained. The method of producing lactate may include collecting or isolating lactate from the culture.

The collecting of lactate from the culture may be performed by using a separation and purification method known in the art. The collecting of lactate may be performed by centrifugation, ion-exchange chromatography, filtration, precipitation, extraction, distillation, or combination thereof. For example, the culture may be centrifuged to separate biomass, and a supernatant thus obtained may be separated by ion-exchange chromatography.

The yeast cell according to an aspect of the present invention may be acid-resistant, and lactate may be produced at a high concentration and a high yield.

Lactate may be produced at a high concentration and a high yield by using the method of producing lactate according to another aspect of the present invention.

Hereinafter, the present invention is described in greater detail with reference to embodiments. However, the embodiments are for illustrative purposes only and do not limit the scope of the present invention.

Example 1. Manufacture of Strain and Manufacture of Expression Vector for Effective Production of Lactate 1.1 Manufacture of *Saccharomyces cerevisiae* Strain in which Pdc1, Cyb2, and Gpd1 Genes are Deleted and an Exogenous Ldh Gene Introduced

*Saccharomyces cerevisiae* CEN.PK2-1D (MATαura3-52; trp1-289; leu2-3, 112; his3Δ1; MAL2-8C; SUC2, EUROS-CARF accession number: 30000B) was used as a lactate production strain, and *Saccharomyces cerevisiae* CEN.PK2-1D Δpdc1::ldh Δcyb2::ldhΔgpd1::ldh (KCTC 12415BP), in which a pyruvate decarboxylase (pdc1) gene that is a main enzyme of alcohol fermentation, a NAD-dependent glycerol-3-phosphate dehydrogenase (gpd1) gene that is a main enzyme of glycerol biosynthesis, and a L-lactate cytochrome-c oxidoreductase 2 (cyb2) gene that is a lactate decomposition enzyme are deleted and disrupted and a lactate dehydrogenase gene is introduced at a location of each of the genes, was used to block production pathways of main by-products such as ethanol and glycerol.

1.1.1 Preparation of L-LDH Overexpression Vector

A CCW12 promoter PCR fragment obtained by performing PCR with a genomic DNA of *Saccharomyces cerevisiae* CEN.PK2-1D as a template and primers of SEQ ID NOS: 25 and 26 was digested with SacI and XbaI, and the resultant was introduced into a p416-GPD (http://www.atcc.org/products/all/87360.aspx) vector, from which a GPD promoter was digested with SacI and XbaI, thereby producing a p416-CCW12p vector for overexpression of L-ldh.

Figure 2:
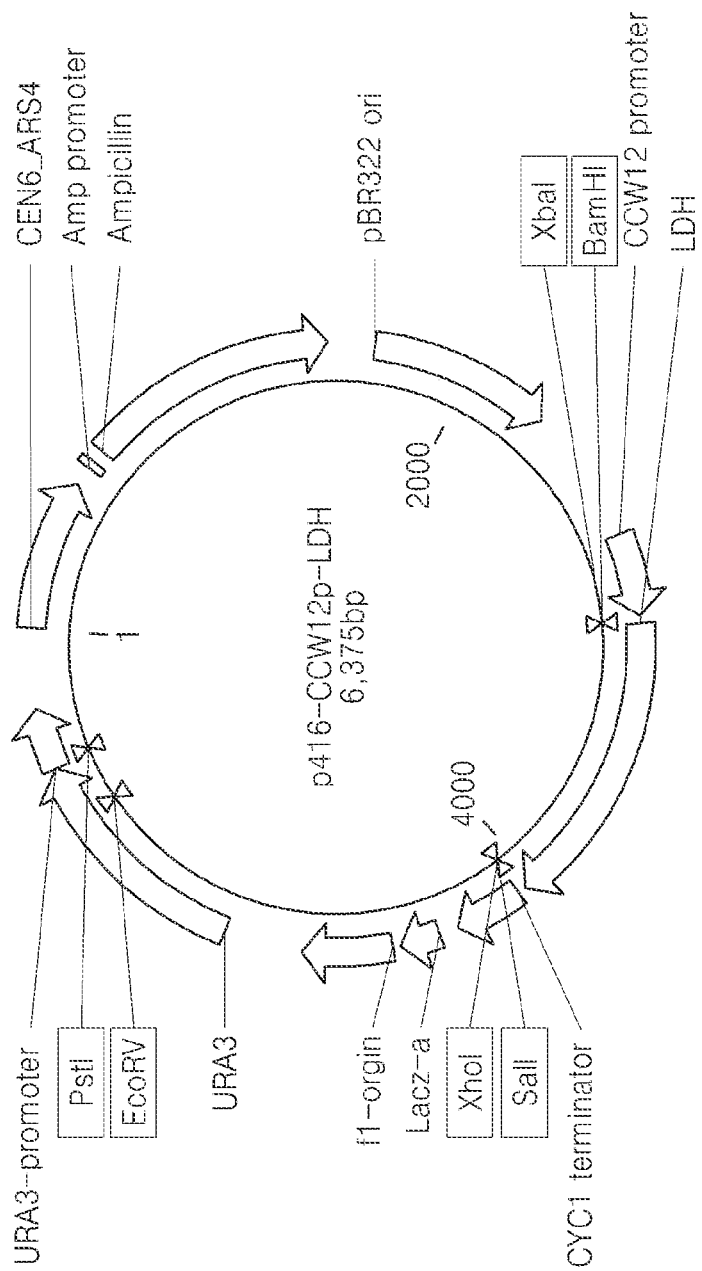
FIG. 2 is a vector map of a p416-CCW12p-LDH vector.

Then, PCR was performed using a genomic DNA of L-ldh gene (SEQ ID NO: 7) derived from *Pelodiscus sinensis japonicus* as a template and primers of SEQ ID NOs: 27 and 28. The PCR fragment thus obtained and the p416-CCW12p prepared as described above were digested with BamHI and SalI, and ligated, thereby producing p416-CCW12p-LDH, which is a L-ldh expression vector. The L-ldh expression vector had a yeast autonomous replication sequence/a yeast centrometric sequence of SEQ ID NO: 18, a CCW12 promoter of SEQ ID NO: 22, and a CYC1 terminator of SEQ ID NO: 24. The L-ldh expression vector included a polynucleotide of SEQ ID NO: 3 encoding L-ldh derived from *Pelodiscus sinensis japonicus*. FIG. 2 is a view illustrating a p416-CCW12p-LDH vector.

1.1.2 Preparation of Introduction Vector for L-Ldh Gene into a Genome

In order to increase production of lactate by enhancing redox balance or engineering glycolysis pathways, L-ldh was additionally introduced into a genome of a strain of KCTC12415BP. In order to introduce the L-ldh gene into the genome of KCTC12415BP, a gene-introduction vector was prepared as follows.

Figure 3:
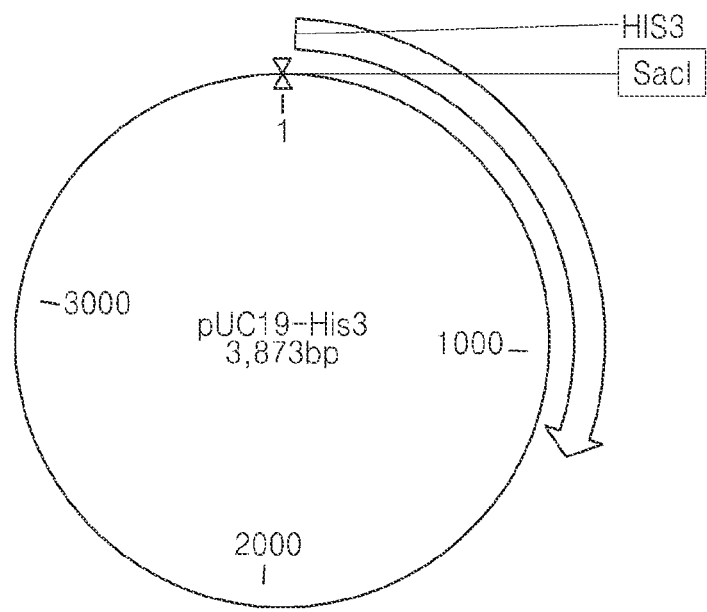
FIG. 3 is a vector map of a pUC19-HIS3 vector.
Figure 4:
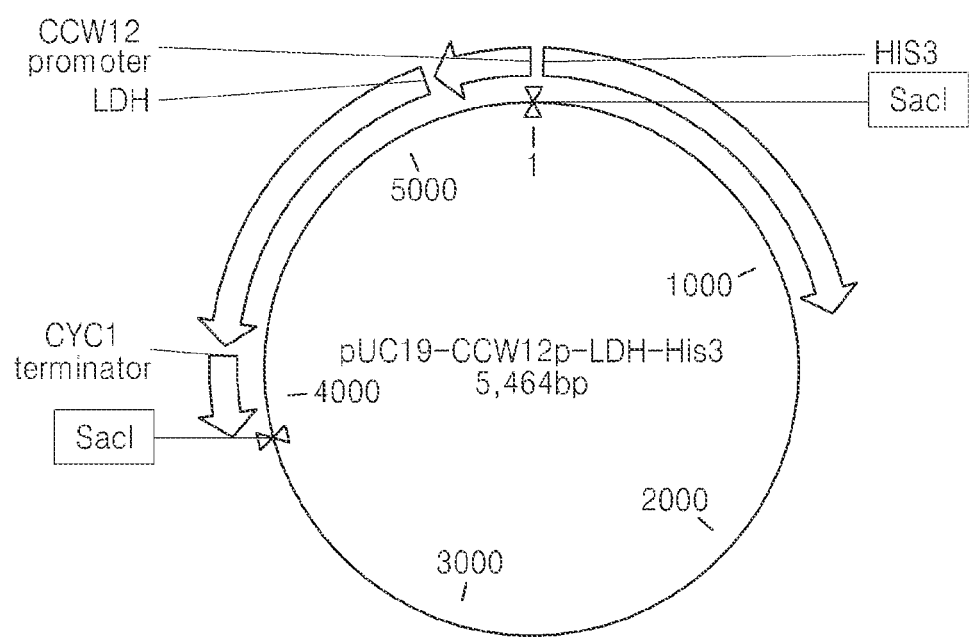
FIG. 4 is a vector map of a pUC19-CCW12p-LDH-HIS3 vector.

In this regard, PCR was performed by using the prepared p416-CCW12p-LDH as a template and primers of SEQ ID NOS: 29 and 30, the resulting PCR fragment and a pUC19-HIS3 (Appl Environ Microbiol. 2002 May; 68(5):2095-100, FIG. 3) vector prepared in advance were digested with SacI and ligated, producing a pUC19-CCW12p-LDH-HIS3 (FIG. 4). PCR was performed by using the pUC19-CCW12p-LDH-HIS3 as a template and primers of SEQ ID NOS: 31 and 32 to prepare a cassette to be inserted to a location of TRP1. The expression cassette including L-ldh may be inserted to a locus of TRP1 gene, and in this case, as the TRP1 gene is deleted, the L-ldh may be inserted to the locus. A mutation strain to which L-ldh is inserted was prepared as follows.

A KCTC12415BP strain was plated onto a YPD agar plate (including 10 g/L of yeast extract, 20 g/L of peptone, and 20 g/L of glucose, and 20 g/L of agar) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and incubated in an incubator at a rate of about 230 rpm and at 30° C.

After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the cells were harvested by performing centrifugation at a rate of about 4,500 rpm for about 10 minutes, resuspended in a lithium acetate solution at a concentration of about 1 M including about 15% of glycerol.

In order to express L-ldh at the same time deleting TRP1, the cassette including L-ldh was mixed with 50% of polyethylene glycol and a single stranded carrier DNA, added to 100 μl of the resuspended competent cell, and reacted in a water tub for about 1 hour at 42° C., and then, the culture solution was spread on a histidine-free minimal agar plate (YSD, containing 6.7 g/L of yeast nitrogen base without amino acids, 1.4 g/L of yeast synthetic drop-out without histidine (Sigma-Aldrich: Cat. no. Y1751), 20 g/L glucose, and 20 g/L of agar) and grown for about 24 hours or more at 30° C. Ten colonies (mutant strains) grown on the plate were selected, patched onto the fresh YSD (−his) minimal agar plate, and at the same time, inoculated into a YSD (−his) liquid medium to isolate the genomic DNA from the above mutant strains by using a commonly used kit (Gentra Puregene Cell kit, Qiagen, USA). In order to confirm deletion of TRP1, PCR was performed by using the genomic DNA of the isolated mutant strain as a template and primers of SEQ ID NOS: 33 and 34, and then, electrophoresis was performed on the obtained PCR product, and thus insertion of the L-ldh expression cassette was confirmed. As a result, Δtrp1::ldh strain (KCTC12415BP Δtrp1::ldh) was obtained.

Figure 5:
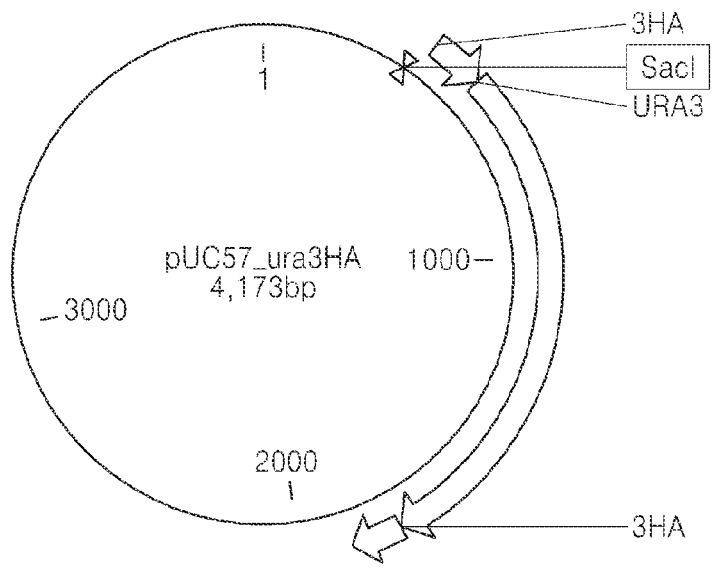
FIG. 5 is a vector map of a pUC57-ura3HA vector.
Figure 6:
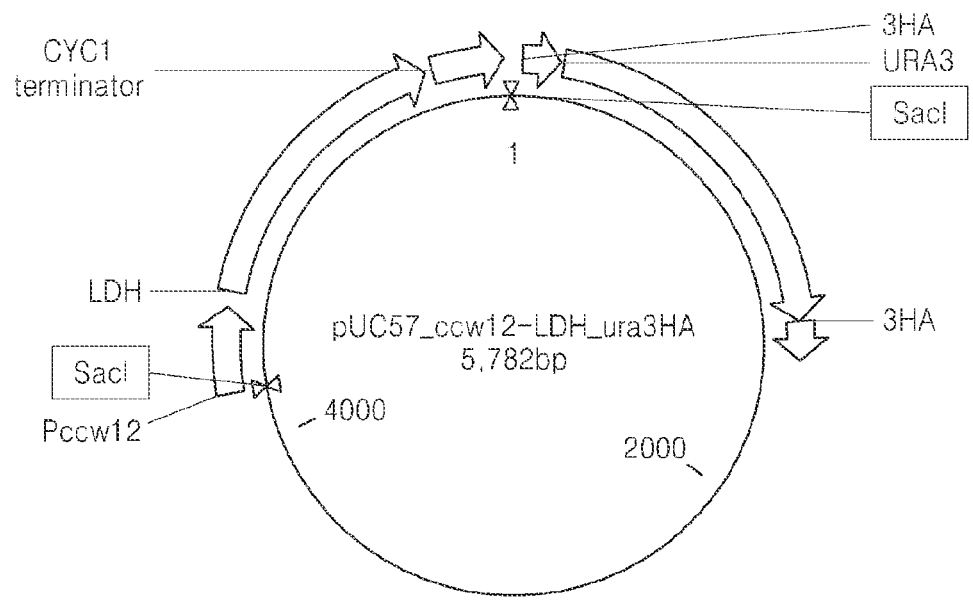
FIG. 6 is a vector map of a pUC57-CCW12-LDH-ura3HA vector.
Figure 7A:
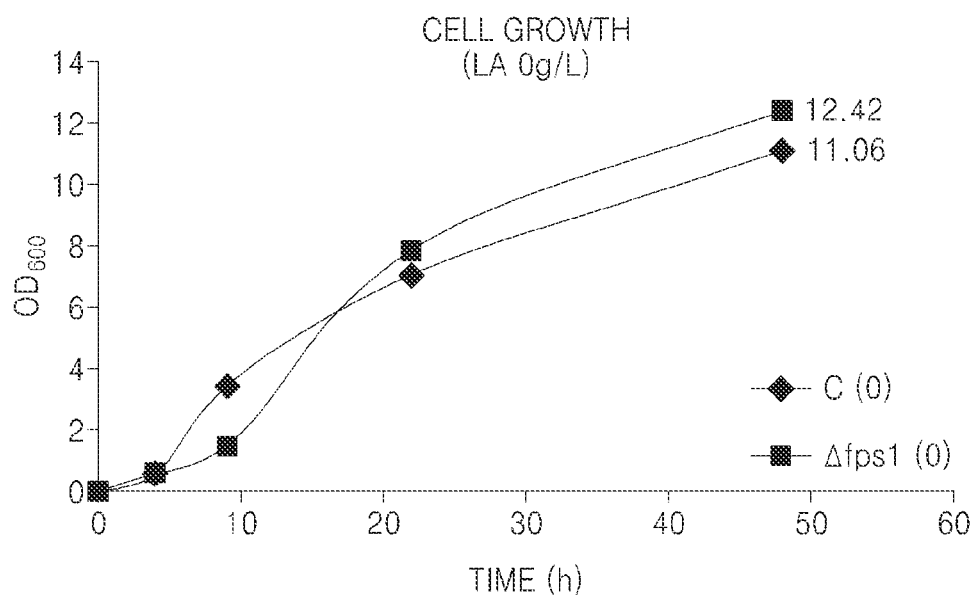
FIGS. 7A to 7E are a series of graphs illustrating cell growth of a Δfps1 strain and a Δnde1Δnde2 (C) strain at different concentrations of lactic acid in the cell culture medium.
Figure 7B:
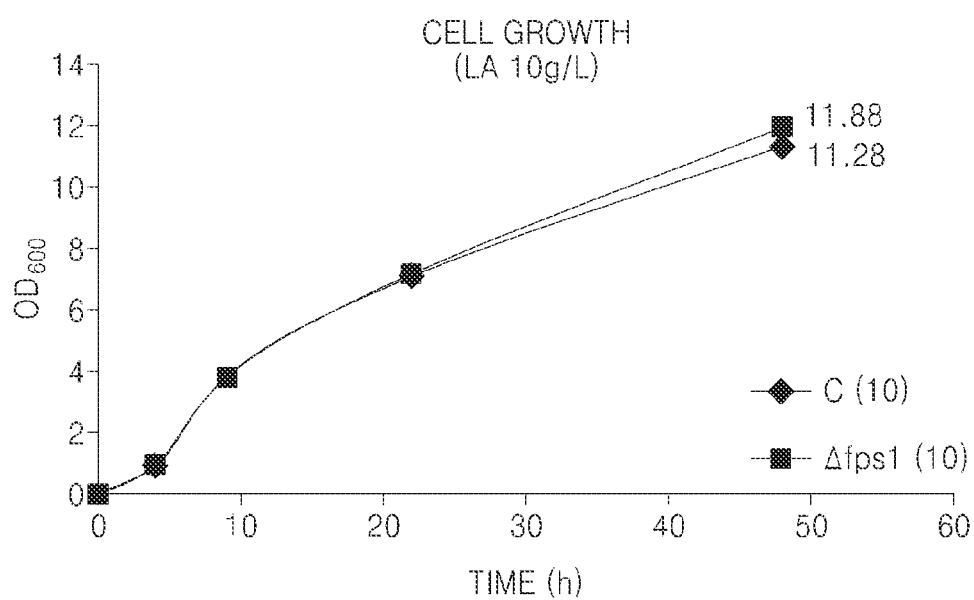
Figure 7C:
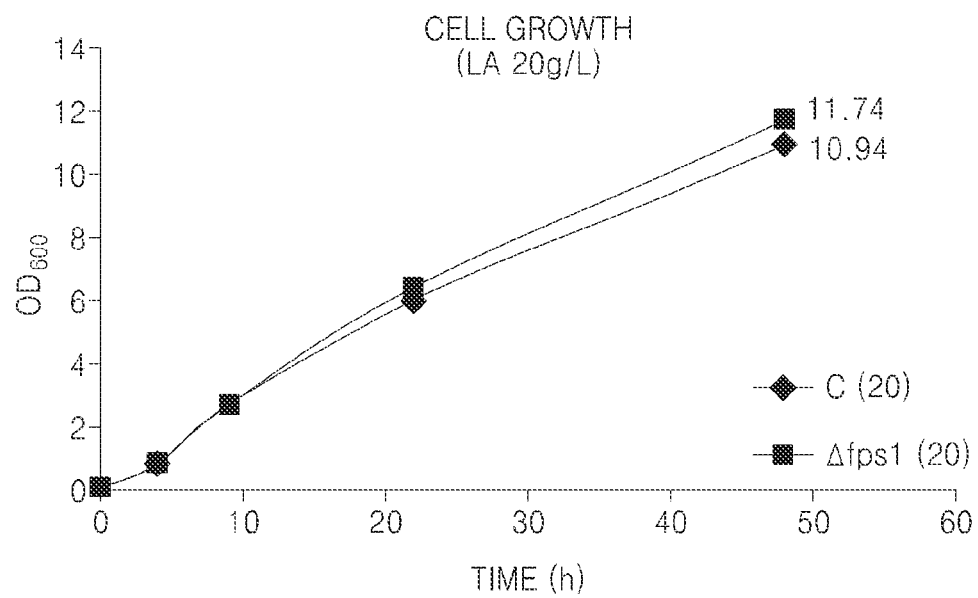
Figure 7D:
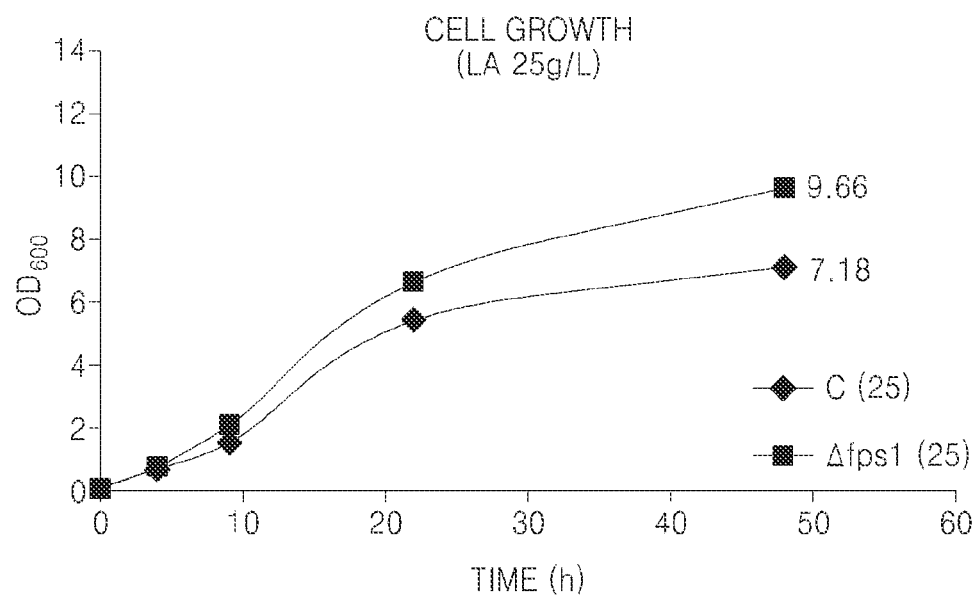
Figure 7E:
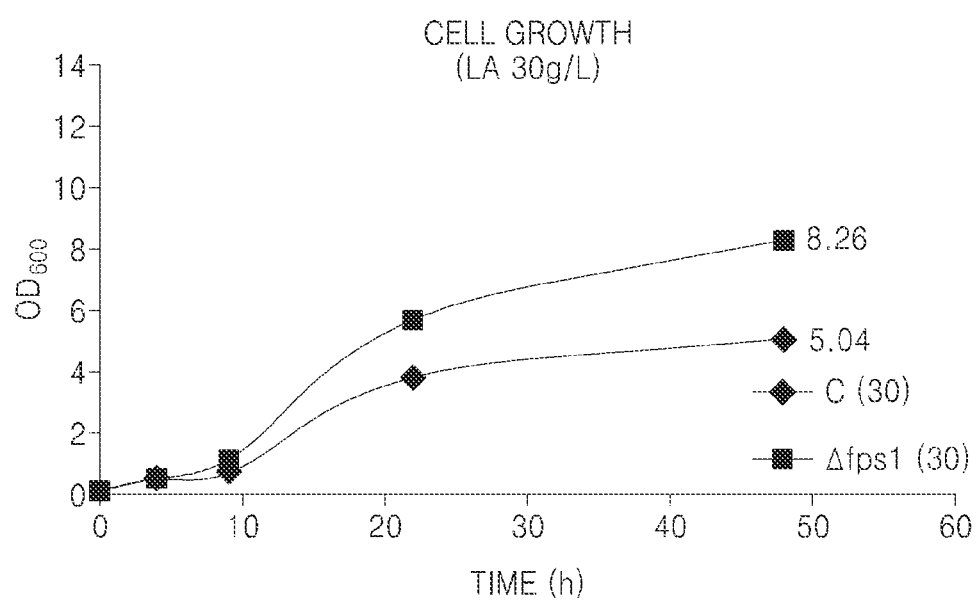

1.2 Preparation of *Saccharomyces cerevisiae* Strain in which Nde1 and Nde2 are Deleted 1.2.1 Preparation of Nde1 Gene Deletion Cassette In order to prepare the nde1 gene deletion cassette, PCR was performed by using the prepared pUC57-ura3HA (FIG. 5) as a template and primers of SEQ ID NOs: 35 and 36.

1.2.2 Preparation of *Saccharomyces cerevisiae* Strain in which Nde1 is Deleted

A mutant strain prepared by deleting nde1 from the Δtrp1::ldh strain (KCTC12415BPΔtrp1::ldh) was manufactured as follows.

A Δtrp1::ldh strain (KCTC12415BPΔtrp1::ldh) was spread on a YPD agar plate (10 g/L of yeast extract, 20 g/L of peptone, 20 g/L of glucose, and 20 g/L of agar)) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and incubated in an incubator at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the cells were harvested by performing centrifugation at a rate of about 4,500 rpm for about 10 minutes, resuspended in a lithium acetate solution at a concentration of about 1 M including about 15% of glycerol.

In order to delete NDE1 gene, the prepared NDE1 gene deletion cassette was mixed with 50% of polyethylene glycol and a single stranded carrier DNA, added to 100 μl of the resuspended competent cell, and reacted in a water tub for about 1 hour at 42° C., and then, the culture solution was spread on a uracil-free minimal agar plate (YSD, containing 6.7 g/L of yeast nitrogen base without amino acids, 1.4 g/L of yeast synthetic drop-out without uracil, 20 g/L glucose, and 20 g/L of agar) and grown for about 24 hours or more at 30° C. Ten colonies (mutant strains) grown on the plate were selected, patched onto the fresh YSD (−ura) minimal agar plate, and at the same time, inoculated into a YSD (−ura) liquid medium to isolate the genomic DNA from the above mutant strains by using a commonly used kit (Gentra Puregene Cell kit, Qiagen, USA). In order to confirm deletion of nde1, PCR was performed by using the genomic DNA of the isolated mutant strain as a template and primers of SEQ ID NOS: 37 and 38, and then, electrophoresis was performed on the obtained PCR product. As a result, KCTC12415BPΔtrp1::ldhΔnde1+ura3 was obtained.

Also, in order to delete an additional gene by using the gene deletion vector, URA3 gene, which is a selection marker used for deletion of nde1, was deleted by using an URA3 pop-out method. That is, KCTC12415BPΔtrp1:ldhΔnde1+ura3 was inoculated in about 10 ml of a YPD liquid medium and cultured for about 18 hours at 30° C., was spread on a 5-FOA agar plate (YSD, containing 6.7 g/L of yeast nitrogen base without amino acids, 1.4 g/L of yeast synthetic drop-out, 20 g/L glucose, 1 μg/L of 5-fluoroorotic acid, and 20 g/L agar) and grown for about 24 hours or more at 30° C. Ten colonies (URA3 pop-out strains) grown on the 5-FOA plate were selected, patched onto the fresh 5-FOA agar plate, and at the same time, inoculated into a YPD liquid medium to isolate the genomic DNA from the above strains by using a commonly used kit (Gentra Puregene Cell kit, Qiagen, USA). In order to confirm deletion of URA3, PCR was performed by using the genomic DNA of the isolated URA3 pop-out strain as a template and primers of SEQ ID NOS: 37 and 38, and then, electrophoresis was performed on the obtained PCR product. As a result, Δnde1 strain (KCTC12415BP Δtrp1::ldhΔnde1) was obtained.

1.2.3 Preparation of Nde2 Gene Deletion Cassette

In order to prepare the nde2 gene deletion cassette, PCR was performed by using the prepared pUC57-ura3HA (FIG. 5) as a template and primers of SEQ ID NOS: 39 and 40.

1.2.4 Preparation of *Saccharomyces cerevisiae* Strain in which Nde1 and Nde2 are Deleted A mutant strain prepared by deleting nde2 from the Δnde1 strain (KCTC12415BPΔtrp1::ldhΔnde1) was manufactured as follows.

A competent cell was obtained by treating the Δnde1 strain with a lithium acetate solution in the same manner as in Example 1.2.2.

In order to delete nde2 gene, the nde2 gene deletion cassette prepared in Example 1.2.3 was mixed with 50% of polyethylene glycol and a single stranded carrier DNA, added to 100 ul of the resuspended competent cell, and reacted in the same manner performed in Example 1.2.2, and thus colonies were obtained on a YSD (−ura) minimal agar plate. Ten colonies (mutant strains) grown on the plate were selected, patched onto the fresh YSD (−ura) minimal agar plate, and at the same time, inoculated into a YSD (−ura) liquid medium to isolate the genomic DNA from the above mutant strains by using a commonly used kit (Gentra Puregene Cell kit, Qiagen, USA). In order to confirm deletion of nde2, PCR was performed by using the genomic DNA of the isolated mutant strain as a template and primers of SEQ ID NOS: 41 and 42, and then, electrophoresis was performed on the obtained PCR product. As a result, KCTC12415BPΔtrp1::ldhΔnde1Δnde2+ura3 was obtained.

Also, in order to delete an additional gene by using the gene deletion vector, URA3 gene, which is a selection marker used for deletion of nde2, was deleted from *Saccharomyces cerevisiae* KCTC12415BP Δtrp1:ldhΔnde1Δnde2+ura3 in the same manner as in Example 1.2.2. In order to confirm deletion of URA3, PCR was performed by using a genomic DNA of the separated URA3 pop-out strain as a template and primers of SEQ ID NOs: 41 and 42, and then, electrophoresis was performed on the obtained PCR product. As a result, a Δnde1Δnde2 strain (KCTC12415BPΔtrp1::ldhΔnde1Δnde2) was obtained.

Example 2. Preparation of *Saccharomyces Cerevisiae* Strain in which Fps1 is Deleted 2.1 Preparation of Fps1 Gene Deletion Cassette In order to delete fps1 gene by using a homogenous recombination method, PCR was performed by using the pUC57-ura3HA shown in FIG. 5 as a template and primers (fps1_del_F, fps1_del_R) of SEQ ID NOS: 43 and 44 to prepare a fps1 gene deletion cassette.

2.2 Preparation of *Saccharomyces cerevisiae* Strain in which Fps1 is Deleted

A mutant strain prepared by deleting fps1 from the Δnde1Δnde2 strain (KCTC12415BPΔtrp1::ldhΔnde1Δnde2) was manufactured as follows.

A competent cell was obtained by treating the Δnde1Δnde2 strain with a lithium acetate solution in the same manner as in Example 1.2.2.

In order to delete fps1 gene, the fps1 gene deletion cassette prepared in Example 2.1 was mixed with 50% of polyethylene glycol and a single stranded carrier DNA, added to 100 μl of the resuspended competent cell, and reacted in the same manner performed in Example 1.2.2, and thus colonies were obtained on a YSD (−ura) minimal agar plate. Ten colonies (mutant strains) grown on the plate were selected, patched onto the fresh YSD (−ura) minimal agar plate, and at the same time, inoculated into a YSD (−ura) liquid medium to isolate the genomic DNA from the above mutant strains by using a commonly used kit (Gentra Puregene Cell kit, Qiagen, USA). In order to confirm deletion of fps1, PCR was performed by using the genomic DNA of the isolated mutant strain as a template and primers (fps1_F, fps1_R) of SEQ ID NOs: 45 and 46, and then, electrophoresis was performed on the obtained PCR product. As a result, KCTC12415BPΔtrp1::ldhΔnde1Δnde2Δfps1+ura3 was obtained.

Also, in order to delete an additional gene, URA3 gene, which is a selection marker used for deletion of fps1, was deleted from Saccharomyces cerevisiae KCTC12415BPΔtrp1:ldhΔnde1Δnde2Δfps1+ura3 by using the URA3 pop-out method in the same manner as in Example 1.2.2. In order to confirm deletion of URA3, PCR was performed by using a genomic DNA of the separated URA3 pop-out strain as a template and primers of SEQ ID NOS: 45 and 46, and then, electrophoresis was performed on the obtained PCR product. As a result, a Δfps1 strain (KCTC12415BPΔtrp1::ldhΔnde1Δnde2Δfps1) was obtained.

Example 3. Measurement of Acid-Resistant Property of Strain in which Fps1 Gene is Deleted Each of the Δnde1Δnde2 strain and the Δfps1 strain prepared in Examples 1 and 2 were spread on a YPD agar plate and grown for about 24 hours or more at 30° C., inoculated into 50 ml of YPD including about 0 to about 30 g/L of lactic acid and 40 g/L of glucose, and incubated in an anaerobic condition for about 48 hours or more at 30° C. Periodically, the culture was obtained from the flask during the culturing, and a cell concentration was measured at $OD_{600}$ nm.

FIGS. 7A to 7E illustrate cell growth of the Δfps1 strain and Δnde1Δnde2 strain (C) according to a concentration of lactic acid included in the medium. As shown in FIGS. 7A to 7E, when an amount of the included lactic acid increases, an $OD_{600}$ value of the Δfps1 strain is higher than that of the Δnde1Δnde2 strain (C). These results demonstrate that a Fps1 gene-deleted yeast cell allows an amount of glycerol to be increased in the cell and provides better acid-resistant property and improved growth under an acid condition compared to a yeast cell in which a Fps1 gene is not deleted.

Example 4. Production of Lactate Using a Fps1-Deleted Strain

Each of the Δnde1Δnde2 strain and the Δfps1 strain prepared in Examples 1 and 2 were spread on a YPD agar plate and grown for about 24 hours or more at 30° C., inoculated into 50 ml of a YPD liquid medium including 40 g/L of glucose, and incubated in an aerobic condition for about 16 hours or more at 30° C. Fermentation was performed by quantifying an amount of a cell concentration in 50 ml of the strain culture solution when its absorbance is 5.0 at 600 nm by using a spectrophotometer, centrifuging the quantified result, removing the supernatant, resuspending the cell, and re-inoculating the cell into 50 ml of a fresh YPD liquid medium including 80 g/L of glucose. Conditions for the fermentation included maintaining a rate of about 90 rpm of a stirring incubator for about 24 hours or more at 30° C. During the fermentation, samples were periodically obtained from the flask, and the obtained samples were centrifuged at a rate of about 13,000 rpm, and then, a concentration of lactate of the supernatant was analyzed by using a liquid chromatography (HPLC).

As shown in Table 1, an $OD_{600}$ value of the Δfps1 strain was greater than that of the Δnde1Δnde2 strain (15.22 vs. 15.62); L-lactate producing capability of the Δfps1 strain was increased compared to the Δnde1Δnde2 strain (33.9 g/L vs 35.3 g/L); and yield of the Δfps1 strain was increased compared to the Δnde1Δnde2 strain (43.4% vs. 46.6%). Thus, lactate production and yield may increase in a fps1 gene-deleted strain. Also, the fps1 gene-deleted strain may have an improved metabolic pathway as well as a high cell growth rate in a high lactate concentration, and thus lactate production and yield may increase in the strain.

TABLE 1

| Strain | Characteristic | $OD_{600}$ | LA (g/L) | Yield (%) |
|---|---|---|---|---|
| Δnde1Δnde2 | KCTC12415BPΔtrp1::ldhΔnde1Δnde2 | 15.22 | 33.9 | 43.4 |
| Δfps1 strain | KCTC12415BPΔtrp1::ldhΔnde1Δnde2Δfps1 | 15.62 | 35.3 | 46.6 |

50 ml flask, culturing time: about 25 hours, and LA: lactate

Accession Number: KCTC 12415BP was deposited at the Korean Collection for Type Cultures (KTCT) on May 30, 2013.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A lactic acid-resistant yeast cell comprising a genetic modification that reduces aquaglyceroporin (Fps1) activity in the acid-resistant yeast cell compared to that of a parent cell without the genetic modification wherein the yeast cell comprises a polypeptide that converts pyruvate to lactic acid.

2. The acid-resistant yeast cell of claim 1, wherein the genetic modification is a deletion or disruption mutation of a polynucleotide that encodes the Fps1.

3. The acid-resistant yeast cell of claim 1, wherein the Fps1 is a polypeptide having at least 95% sequence identity with SEQ ID NO: 1.

4. The acid-resistant yeast cell of claim 1, wherein the polynucleotide that encodes the Fps1 has a polynucleotide sequence that encodes an amino acid sequence having at least 95% sequence identity with SEQ ID NO: 1, or that has at least 95% sequence identity to SEQ ID NO: 2.

5. The acid-resistant yeast cell of claim 1, wherein the acid-resistant yeast cell is resistant under a pH condition of about 2 to about 4.5.

6. The acid-resistant yeast cell of claim 1, wherein the yeast cell is Saccharomyces genus, Kluyveromyces genus, Candida genus, Pichia genus, Issatchenkia genus, Debaryomyces genus, Zygosaccharomyces genus, Shizosaccharomyces genus, or Saccharomycopsis genus.

7. The acid-resistant yeast cell of claim 1, wherein the yeast cell is Saccharomyces cerevisiae.

8. The acid-resistant yeast cell of claim 1, wherein the yeast cell comprises a polynucleotide that encodes a lactate dehydrogenase.

9. The acid-resistant yeast cell of claim 1, wherein the polypeptide that converts pyruvate to lactate has at least 95% sequence identity with SEQ ID NO: 3.

10. The acid-resistant yeast cell of claim 8, wherein expression or activity of the lactate dehydrogenase is increased in the acid-resistant yeast cell compared to a parent cell.

11. The acid-resistant yeast cell of claim 1, wherein activity of a polypeptide that converts pyruvate to acetaldehyde, a polypeptide that converts lactate to pyruvate, a polypeptide that converts dehydroxyacetone phosphate (DHAP) to glycerol-3-phosphate, an external mitochondrial NADH dehydrogenase, or a combination thereof is reduced in the acid-resistant yeast cell compared to a parent cell.

12. The acid-resistant yeast cell of claim 11, wherein the yeast cell comprises an exogenous polynucleotide encoding lactate dehydrogenase.

13. The acid-resistant yeast cell of claim 1, wherein the acid-resistant yeast cell comprises a deletion or disruption mutation of a gene encoding a polypeptide that converts pyruvate to acetaldehyde, a gene encoding a polypeptide that converts lactate to pyruvate, a gene encoding a polypeptide that converts dehydroxyacetone phosphate (DHAP) to glycerol-3-phosphate, a gene encoding an external mitochondrial NADH dehydrogenase, or a combination thereof.

14. The acid-resistant yeast cell of claim 11, wherein the polypeptide that converts pyruvate to acetaldehyde, the polypeptide that converts lactate to pyruvate, the polypeptide that converts dehydroxyacetone phosphate (DHAP) to glycerol-3-phosphate, and the external mitochondrial NADH dehydrogenase each comprise an amino acid sequence having at least 95% of sequence identity with SEQ ID NO: 8, 10, 12, 14, or 16, respectively.

15. A method of producing lactate, wherein the method comprises culturing the acid-resistant yeast cell of claim 1 in a cell culture medium, whereby the yeast cell produces lactate.

16. The method of claim 15, wherein the method further comprises collecting lactate from the cell culture medium.

17. The method of claim 15, wherein the culturing of the yeast cell is performed under a microaerobic or anaerobic condition.

18. The method of claim 15, wherein the culturing of the yeast cell is performed under a pH condition of about 2 to about 7.

19. A method of increasing the acid-resistance of a yeast cell, the method comprising deleting or disrupting expression of a polynucleotide that encodes the Fps1 in a yeast cell to increase the acid-resistance of the yeast cell.

20. The acid-resistant yeast cell of claim 1, wherein the cell produces more lactic acid compared to the parent cell.

* * * * *

SEQUENCE LISTING

```
<160> NUMBER OF SEQ ID NOS: 46

<210> SEQ ID NO 1
<211> LENGTH: 669
<212> TYPE: PRT
<213> ORGANISM: Saccharomyces cerevisiae

<400> SEQUENCE: 1

Met Ser Asn Pro Gln Lys Ala Leu Asn Asp Phe Leu Ser Ser Glu Ser
  1               5                  10                  15

Val His Thr His Asp Ser Ser Arg Lys Gln Ser Asn Lys Gln Ser Ser
             20                  25                  30

Asp Glu Gly Arg Ser Ser Ser Gln Pro Ser His His His Ser Gly Gly
         35                  40                  45

Thr Asn Asn Asn Asn Asn Asn Asn Asn Asn Asn Asn Ser Asn Asn
     50                  55                  60

Asn Asn Asn Gly Asn Asp Gly Gly Asn Asp Asp Asp Tyr Asp Tyr Glu
 65                  70                  75                  80

Met Gln Asp Tyr Arg Pro Ser Pro Gln Ser Ala Arg Pro Thr Pro Thr
                 85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
    130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Thr Gly Ala Gln Thr Asn Met Glu
        195                 200                 205

Ser Asn Glu Ser Pro Arg Asn Val Pro Ile Met Val Lys Pro Lys Thr
    210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
                245                 250                 255

Leu Ala Glu Phe Met Gly Thr Met Val Met Ile Ile Phe Gly Ser Ala
            260                 265                 270
```

Val Val Cys Gln Val Asn Val Ala Gly Lys Ile Gln Gln Asp Asn Phe
        275                 280                 285

Asn Val Ala Leu Asp Asn Leu Asn Val Thr Gly Ser Ser Ala Glu Thr
        290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Ala Val Val Met
                325                 330                 335

Gly Tyr Phe Cys Ala Gly Gly Ser Ala Ile Ser Gly Ala His Leu Asn
                340                 345                 350

Pro Ser Ile Thr Leu Ala Asn Leu Val Tyr Arg Gly Phe Pro Leu Lys
        355                 360                 365

Lys Val Pro Tyr Tyr Phe Ala Gly Gln Leu Ile Gly Ala Phe Thr Gly
        370                 375                 380

Ala Leu Ile Leu Phe Ile Trp Tyr Lys Arg Val Leu Gln Glu Ala Tyr
385                 390                 395                 400

Ser Asp Trp Trp Met Asn Glu Ser Val Ala Gly Met Phe Cys Val Phe
                405                 410                 415

Pro Lys Pro Tyr Leu Ser Ser Gly Arg Gln Phe Phe Ser Glu Phe Leu
        420                 425                 430

Cys Gly Ala Met Leu Gln Ala Gly Thr Phe Ala Leu Thr Asp Pro Tyr
        435                 440                 445

Thr Cys Leu Ser Ser Asp Val Phe Pro Leu Met Met Phe Ile Leu Ile
        450                 455                 460

Phe Ile Ile Asn Ala Ser Met Ala Tyr Gln Thr Gly Thr Ala Met Asn
465                 470                 475                 480

Leu Ala Arg Asp Leu Gly Pro Arg Leu Ala Leu Tyr Ala Val Gly Phe
                485                 490                 495

Asp His Lys Met Leu Trp Val His His His Phe Phe Trp Val Pro
                500                 505                 510

Met Val Gly Pro Phe Ile Gly Ala Leu Met Gly Gly Leu Val Tyr Asp
        515                 520                 525

Val Cys Ile Tyr Gln Gly His Glu Ser Pro Val Asn Trp Ser Leu Pro
        530                 535                 540

Val Tyr Lys Glu Met Ile Met Arg Ala Trp Phe Arg Arg Pro Gly Trp
545                 550                 555                 560

Lys Lys Arg Asn Arg Ala Arg Arg Thr Ser Asp Leu Ser Asp Phe Ser
                565                 570                 575

Tyr Asn Asn Asp Asp Asp Glu Glu Phe Gly Glu Arg Met Ala Leu Gln
                580                 585                 590

Lys Thr Lys Thr Lys Ser Ser Ile Ser Asp Asn Glu Asn Glu Ala Gly
        595                 600                 605

Glu Lys Lys Val Gln Phe Lys Ser Val Gln Arg Gly Lys Arg Thr Phe
        610                 615                 620

Gly Gly Ile Pro Thr Ile Leu Glu Glu Glu Asp Ser Ile Glu Thr Ala
625                 630                 635                 640

Ser Leu Gly Ala Thr Thr Thr Asp Ser Ile Gly Leu Ser Asp Thr Ser
                645                 650                 655

Ser Glu Asp Ser His Tyr Gly Asn Ala Lys Lys Val Thr
                660                 665

<210> SEQ ID NO 2
<211> LENGTH: 2010

<212> TYPE: DNA
<213> ORGANISM: Saccharomyces cerevisiae

<400> SEQUENCE: 2

```
atgagtaatc ctcaaaaagc tctaaacgac tttctgtcca gtgaatctgt tcatacacat      60
gatagttcta ggaaacaatc taataagcag tcatccgacg aaggacgctc ttcatcacaa     120
ccttcacatc atcactctgg tggtactaac aacaataata acaataataa taataataat     180
aacagtaaca acaacaacaa cggcaacgat gggggaaatg atgacgacta tgattatgaa     240
atgcaagatt atagaccttc tccgcaaagt gcgcggccta ctcccacgta tgttccacaa     300
tattctgtag aaagtgggac tgctttcccg attcaagagg ttattcctag cgcatacatt     360
aacacacaag atataaacca taaagataac ggtccgccga gtgcaagcag taatagagca     420
ttcaggccta gagggcagac cacagtgtcg gccaacgtgc ttaacattga agattttac      480
aaaaatgcag acgatgcgca taccatcccg gagtcacatt tatcgagaag gagaagtagg     540
tcgagggcta cgagtaatgc tgggcacagt gccaatacag cgccacgaa tggcaggact      600
actggtgccc aaactaatat ggaaagcaat gaatcaccac gtaacgtccc cattatggtg     660
aagccaaaga cattatacca gaaccctcaa acacctacag tcttgccctc cataccat      720
ccaattaata aatggtcttc cgtcaaaaac acttatttga aggaattttt agccgagttt     780
atgggaacaa tggttatgat tattttcggt agtgctgttg tttgtcaggt caatgttgct     840
gggaaaatac agcaggacaa tttcaacgtg gctttggata accttaacgt taccgggtct     900
tctgcagaaa cgatagacgc tatgaagagt ttaacatcct tggtttcatc cgttgcgggc     960
ggtacctttg atgatgtggc attgggctgg gctgctgccg tggtgatggg ctatttctgc    1020
gctggtggta gtgccatctc aggtgctcat ttgaatccgt ctattacatt agccaatttg    1080
gtgtatagag gttttcccct gaagaaagtt cctattact ttgctggaca attgatcggt     1140
gccttcacag gcgctttgat cttgttat tggtacaaaa gggtgttaca agaggcatat     1200
agcgattggt ggatgaatga agtgttgcg ggaatgttt gcgttttcc aaagccttat      1260
ctaagttcag gacggcaatt tttttccgaa tttttatgtg gagctatgtt acaagcagga    1320
acatttgcgc tgaccgatcc ttatacgtgt ttgtcctctg atgttttccc attgatgatg    1380
tttatttga ttttcattat caatgcttcc atggcttatc agacaggtac agcaatgaat     1440
ttggctcgtg atctgggccc acgtcttgca ctatatgcag ttggatttga tcataaaatg    1500
ctttgggtgc atcatcatca tttctttgg gttcccatgg taggcccatt tattggtgcg    1560
ttaatggggg ggttggttta cgatgtctgt atttatcagg tcatgaatc tccagtcaac     1620
tggtctttac cagtttataa ggaaatgatt atgagagcct ggtttagaag gcctggttgg    1680
aagaagagaa atagagcaag aagaacatcg gacctgagtg acttctcata caataacgat    1740
gatgatgagg aatttggaga agaatggct cttcaaaaga caaagaccaa gtcatctatt     1800
tcagacaacg aaaatgaagc aggagaaaag aaagtgcaat ttaaatctgt tcagcgcggc    1860
aaaagaacgt ttggtggtat accaacaatt cttgaagaag aagattccat tgaaactgct    1920
tcgctaggtg cgacgacgac tgattctatt gggttatccg acacatcatc agaagattcg    1980
cattatggta atgctaagaa ggtaacatga                                     2010
```

<210> SEQ ID NO 3
<211> LENGTH: 332
<212> TYPE: PRT
<213> ORGANISM: Pelodiscus sinensis japonicus -continued

<400> SEQUENCE: 3

Met Ser Val Lys Glu Leu Leu Ile Gln Asn Val His Lys Glu His
1               5                   10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 4
<211> LENGTH: 332
<212> TYPE: PRT
<213> ORGANISM: Ornithorhynchus anatinus

<400> SEQUENCE: 4

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
            20                  25                  30

```
Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
                100                 105                 110

Asn Val Asn Ile Phe Lys Phe Ile Ile Pro Asn Val Val Lys Tyr Ser
                115                 120                 125

Pro Asn Cys Lys Leu Leu Val Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
                180                 185                 190

His Gly Asp Ser Ser Val Pro Val Trp Ser Gly Val Asn Val Ala Gly
                195                 200                 205

Val Ser Leu Lys Asn Leu His Pro Asp Leu Gly Thr Asp Ala Asp Lys
                210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
                260                 265                 270

Ile Ser Thr Met Ile Lys Gly Leu Tyr Gly Ile Lys Asp Glu Val Phe
                275                 280                 285

Leu Ser Val Pro Cys Val Leu Gly Gln Asn Gly Ile Ser Asp Val Val
                290                 295                 300

Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 5
<211> LENGTH: 332
<212> TYPE: PRT
<213> ORGANISM: Tursiops truncatus

<400> SEQUENCE: 5

Met Ala Thr Val Lys Asp Gln Leu Ile Gln Asn Leu Leu Lys Glu Glu
 1                   5                  10                  15

His Val Pro Gln Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80
```

```
Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 6
<211> LENGTH: 332
<212> TYPE: PRT
<213> ORGANISM: Rattus norvegicus

<400> SEQUENCE: 6

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
```

```
              115                 120                 125
Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 7
<211> LENGTH: 999
<212> TYPE: DNA
<213> ORGANISM: Pelodiscus sinensis japonicus

<400> SEQUENCE: 7
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgttgc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tggagaaaaa attaggtatt     540
cactccttat cttgtcatgg ctggataata ggcgaacatg gtgattcttc ggtacctgtt     600
tggtccgggg ttaatgtggc tggtgttagt ttaaaagcat tatatcctga cctgggtact     660
gatgccgata agaacattg gaagaagtg cacaaacaag tggttgattc tgcttacgaa     720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900
```

```
acagacgtcg tgaagatgac attgaaatca gaggaagagg aaaaactaag aaagtcagcc    960
gatactctgt ggggcattca aaaggaattg cagtttttaa                          999
```

<210> SEQ ID NO 8
<211> LENGTH: 563
<212> TYPE: PRT
<213> ORGANISM: Saccharomyces cerevisiae

<400> SEQUENCE: 8

| | | | | | | | | | | | | | | | |
|---|---|---|---|---|---|---|---|---|---|---|---|---|---|---|---|
| Met | Ser | Glu | Ile | Thr | Leu | Gly | Lys | Tyr | Leu | Phe | Glu | Arg | Leu | Lys | Gln |
| 1 | | | | 5 | | | | | 10 | | | | | 15 | |

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu

```
                355                 360                 365
Trp Met Trp Asn Gln Leu Gly Asn Phe Leu Gln Glu Gly Asp Val Val
    370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
            420                 425                 430
Asp Pro Lys Lys Arg Val Ile Leu Phe Ile Gly Asp Gly Ser Leu Gln
                435                 440                 445
Leu Thr Val Gln Glu Ile Ser Thr Met Ile Arg Trp Gly Leu Lys Pro
    450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
            500                 505                 510
Ala Thr Thr Gly Glu Trp Asp Lys Leu Thr Gln Asp Lys Ser Phe Asn
                515                 520                 525
Asp Asn Ser Lys Ile Arg Met Ile Glu Ile Met Leu Pro Val Phe Asp
    530                 535                 540
Ala Pro Gln Asn Leu Val Glu Gln Ala Lys Leu Thr Ala Ala Thr Asn
545                 550                 555                 560
Ala Lys Gln

<210> SEQ ID NO 9
<211> LENGTH: 1692
<212> TYPE: DNA
<213> ORGANISM: Saccharomyces cerevisiae

<400> SEQUENCE: 9
atgtctgaaa ttactttggg taaatatttg ttcgaaagat taaagcaagt caacgttaac    60
accgttttcg gtttgccagg tgacttcaac ttgtccttgt tggacaagat ctacgaagtt   120
gaaggtatga gatgggctgg taacgccaac gaattgaacg ctgcttacgc cgctgatggt   180
tacgctcgta tcaagggtat gtcttgtatc atcaccacct tcggtgtcgg tgaattgtct   240
gctttgaacg gtattgccgg ttcttacgct gaacacgtcg gtgttttgca cgttgttggt   300
gtcccatcca tctctgctca agctaagcaa ttgttgttgc accacacctt gggtaacggt   360
gacttcactg ttttccacag aatgtctgcc aacatttctg aaaccactgc tatgatcact   420
gacattgcta ccgccccagc tgaaattgac agatgtatca aaccactta cgtcacccaa   480
agaccagtct acttaggttt gccagctaac ttggtcgact tgaacgtccc agctaagttg   540
ttgcaaactc caattgacat gtctttgaag ccaaacgatg ctgaatccga aaaggaagtc   600
attgacacca tcttggcttt ggtcaaggat gctaagaacc cagttatctt ggctgatgct   660
tgttgttcca gacacgacgt caaggctgaa actaagaagt tgattgactt gactcaattc   720
ccagctttcg tcaccccaat gggtaagggt tccattgacg aacaacaccc aagatacggt   780
ggtgtttacg tcggtacctt gtccaagcca gaagttaagg aagccgttga atctgctgac   840
ttgattttgt ctgtcggtgc tttgttgtct gatttcaaca ccggttcttt ctcttactct   900
tacaagacca gaacattgtc gaattccac tccgaccaca tgaagatcag aaacgccact   960
```

```
ttcccaggtg tccaaatgaa attcgttttg caaaagttgt tgaccactat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga accggtacc tccgctttcg gtatcaacca aaccactttc     1200
ccaaacaaca cctacggtat ctctcaagtc ttatggggtt ccattggttt caccactggt    1260
gctaccttgg gtgctgcttt cgctgctgaa gaaattgatc aaagaagag agttatctta    1320 ttcattggtg acggttcttt gcaattgact gttcaagaaa tctccaccat gatcagatgg    1380
ggcttgaagc atacttgtt cgtcttgaac aacgatggtt acaccattga aaagttgatt     1440
cacggtccaa aggctcaata acgaaatt caaggttggg accacctatc cttgttgcca     1500
actttcggtg ctaaggacta tgaaacccac agagtcgcta ccaccggtga atgggacaag   1560
ttgacccaag acaagtcttt caacgacaac tctaagatca gaatgattga aatcatgttg    1620
ccagtcttcg atgctccaca aaacttggtt gaacaagcta agttgactgc tgctaccaac    1680
gctaagcaat aa                                                         1692

<210> SEQ ID NO 10
<211> LENGTH: 591
<212> TYPE: PRT
<213> ORGANISM: Saccharomyces cerevisiae

<400> SEQUENCE: 10

Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
                20                  25                  30

Gly Ser Thr Val Pro Lys Ser Lys Ser Phe Glu Gln Asp Ser Arg Lys
            35                  40                  45

Arg Thr Gln Ser Trp Thr Ala Leu Arg Val Gly Ala Ile Leu Ala Ala
        50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Ile Asn Gly Tyr
                100                 105                 110

Val Tyr Asp Leu Thr Arg Phe Leu Pro Asn His Pro Gly Gly Gln Asp
            115                 120                 125

Val Ile Lys Phe Asn Ala Gly Lys Asp Val Thr Ala Ile Phe Glu Pro
        130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240
```

Tyr His Arg Ile Phe Phe Lys Pro Lys Ile Leu Val Asp Val Arg Lys
              245                 250                 255

Val Asp Ile Ser Thr Asp Met Leu Gly Ser His Val Asp Val Pro Phe
              260                 265                 270

Tyr Val Ser Ala Thr Ala Leu Cys Lys Leu Gly Asn Pro Leu Glu Gly
              275                 280                 285

Glu Lys Asp Val Ala Arg Gly Cys Gly Gln Gly Val Thr Lys Val Pro
              290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
              325                 330                 335

Ser Asp Arg Lys Ile Thr Asp Asp Leu Val Lys Asn Val Glu Lys Leu
              340                 345                 350

Gly Val Lys Ala Leu Phe Val Thr Val Asp Ala Pro Ser Leu Gly Gln
              355                 360                 365

Arg Glu Lys Asp Met Lys Leu Lys Phe Ser Asn Thr Lys Ala Gly Pro
              370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
              405                 410                 415

Glu Leu Lys Lys Lys Thr Lys Leu Pro Ile Val Ile Lys Gly Val Gln
              420                 425                 430

Arg Thr Glu Asp Val Ile Lys Ala Ala Glu Ile Gly Val Ser Gly Val
              435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
              485                 490                 495

Asp Val Leu Lys Ala Leu Cys Leu Gly Ala Lys Gly Val Gly Leu Gly
              500                 505                 510

Arg Pro Phe Leu Tyr Ala Asn Ser Cys Tyr Gly Arg Asn Gly Val Glu
              515                 520                 525

Lys Ala Ile Glu Ile Leu Arg Asp Glu Ile Glu Met Ser Met Arg Leu
              530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
              565                 570                 575

Asn Glu Val Tyr Glu Gly Pro Thr Leu Thr Glu Phe Glu Asp Ala
              580                 585                 590

<210> SEQ ID NO 11
<211> LENGTH: 1776
<212> TYPE: DNA
<213> ORGANISM: Saccharomyces cerevisiae

<400> SEQUENCE: 11
atgctaaaat acaaaccttt actaaaaatc tcgaagaact gtgaggctgc tatcctcaga    60
gcgtctaaga ctagattgaa cacaatccgc gcgtacggtt ctaccgttcc aaaatccaag   120

-continued

```
tcgttcgaac aagactcaag aaaacgcaca cagtcatgga ctgccttgag agtcggtgca    180
attctagccg ctactagttc cgtggcgtat ctaaactggc ataatggcca aatagacaac    240
gagccgaaac tggatatgaa taaacaaaag atttcgcccg ctgaagttgc caagcataac    300
aagcccgatg attgttgggt tgtgatcaat ggttacgtat acgacttaac gcgattccta    360
ccaaatcatc caggtgggca ggatgttatc aagtttaacg ccgggaaaga tgtcactgct    420
attttgaac cactacatgc tcctaatgtc atcgataagt atatagctcc cgagaaaaaa    480
ttgggtcccc ttcaaggatc catgcctcct gaacttgtct gtcctcctta tgctcctggt    540
gaaactaagg aagatatcgc tagaaaagaa caactaaaat cgctgctacc tcctctagat    600
aatattatta acctttacga ctttgaatac ttggcctctc aaactttgac taaacaagcg    660
tgggcctact attcctccgg tgctaacgac gaagttactc acagagaaaa ccataatgct    720
tatcatagga ttttttttcaa accaaagatc cttgtagatg tacgcaaagt agacatttca    780
actgacatgt tgggttctca tgtggatgtt cccttctacg tgtctgctac agctttgtgt    840
aaactgggaa acccccttaga aggtgaaaaa gatgtcgcca gaggttgtgg ccaaggtgtg    900
acaaaagtcc cacaaatgat atctactttg gcttcatgtt cccctgagga aattattgaa    960
gcagcaccct ctgataaaca aattcaatgg taccaactat atgttaactc tgatagaaag   1020
atcactgatg atttggttaa aaatgtagaa aagctgggtg taaaggcatt atttgtcact   1080
gtggatgctc aagtttagg tcaaagagaa aaagatatga agctgaaatt ttccaataca   1140
aaggctggtc caaaagcgat gaagaaaact aatgtagaag aatctcaagg tgcttcgaga   1200
gcgttatcaa agtttattga cccctctttg acttggaaag atatagaaga gttgaagaaa   1260
aagacaaaac tacctattgt tatcaaaggt gttcaacgta ccgaagatgt tatcaaagca   1320
gcagaaatcg gtgtaagtgg ggtggttcta tccaatcatg gtggtagaca attagatttt   1380
tcaagggctc ccattgaagt cctggctgaa accatgccaa tcctggaaca acgtaacttg   1440
aaggataagt tggaagtttt cgtggacggt ggtgttcgtc gtggtacaga tgtcttgaaa   1500
gcgttatgtc taggtgctaa aggtgttggt ttgggtagac cattcttgta tgcgaactca   1560
tgctatggtc gtaatggtgt tgaaaaagcc attgaaattt taagagatga aattgaaatg   1620
tctatgagac tattaggtgt tactagcatt gcggaattga agcctgatct tttagatcta   1680
tcaacactaa aggcaagaac agttggagta ccaaacgacg tgctgtataa tgaagtttat   1740
gagggaccta ctttaacaga atttgaggat gcatga                             1776
```

<210> SEQ ID NO 12
<211> LENGTH: 391
<212> TYPE: PRT
<213> ORGANISM: Saccharomyces cerevisiae

<400> SEQUENCE: 12

```
Met Ser Ala Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
                 20                  25                  30

Lys Pro Phe Lys Val Thr Val Ile Gly Ser Gly Asn Trp Gly Thr Thr
             35                  40                  45

Ile Ala Lys Val Val Ala Glu Asn Cys Lys Gly Tyr Pro Glu Val Phe
         50                  55                  60

Ala Pro Ile Val Gln Met Trp Val Phe Glu Glu Glu Ile Asn Gly Glu
 65                  70                  75                  80
```

```
Lys Leu Thr Glu Ile Ile Asn Thr Arg His Gln Asn Val Lys Tyr Leu
                85                  90                  95
Pro Gly Ile Thr Leu Pro Asp Asn Leu Val Ala Asn Pro Asp Leu Ile
            100                 105                 110
Asp Ser Val Lys Asp Val Asp Ile Ile Val Phe Asn Ile Pro His Gln
        115                 120                 125
Phe Leu Pro Arg Ile Cys Ser Gln Leu Lys Gly His Val Asp Ser His
    130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                165                 170                 175
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
        195                 200                 205
Glu Gly Lys Asp Val Asp His Lys Val Leu Lys Ala Leu Phe His Arg
    210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
    290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
    370                 375                 380
Glu Leu Asp Leu His Glu Asp
385                 390
```

<210> SEQ ID NO 13
<211> LENGTH: 1176
<212> TYPE: DNA
<213> ORGANISM: Saccharomyces cerevisiae

<400> SEQUENCE: 13

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
```

```
atcgttttca acattccaca tcaattttg ccccgtatct gtagccaatt gaaaggtcat    420
gttgattcac acgtcagagc tatctcctgt ctaaagggtt ttgaagttgg tgctaaaggt    480
gtccaattgc tatcctctta catcactgag gaactaggta ttcaatgtgg tgctctatct    540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gacctactt ccacgttagt gtcatcgaag atgttgctgg tatctccatc    720
tgtggtgctt tgaagaacgt tgttgcctta ggttgtggtt cgtcgaagg tctaggctgg    780 ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atggccaatc cgctcaaggt   1020
ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                              1176
```

<210> SEQ ID NO 14
<211> LENGTH: 560
<212> TYPE: PRT
<213> ORGANISM: Saccharomyces cerevisiae

<400> SEQUENCE: 14

```
Met Ile Arg Gln Ser Leu Met Lys Thr Val Trp Ala Asn Ser Ser Arg
  1               5                  10                  15

Phe Ser Leu Gln Ser Lys Ser Gly Leu Val Lys Tyr Ala Lys Asn Arg
             20                  25                  30

Ser Phe His Ala Ala Arg Asn Leu Leu Glu Asp Lys Lys Val Ile Leu
         35                  40                  45

Gln Lys Val Ala Pro Thr Thr Gly Val Val Ala Lys Gln Ser Phe Phe
     50                  55                  60

Lys Arg Thr Gly Lys Phe Thr Leu Lys Ala Leu Leu Tyr Ser Ala Leu
 65                  70                  75                  80

Ala Gly Thr Ala Tyr Val Ser Tyr Ser Leu Tyr Arg Glu Ala Asn Pro
                 85                  90                  95

Ser Thr Gln Val Pro Gln Ser Asp Thr Phe Pro Asn Gly Ser Lys Arg
            100                 105                 110

Lys Thr Leu Val Ile Leu Gly Ser Gly Trp Gly Ser Val Ser Leu Leu
        115                 120                 125

Lys Asn Leu Asp Thr Thr Leu Tyr Asn Val Val Val Ser Pro Arg
    130                 135                 140

Asn Tyr Phe Leu Phe Thr Pro Leu Leu Pro Ser Thr Pro Val Gly Thr
145                 150                 155                 160

Ile Glu Leu Lys Ser Ile Val Glu Pro Val Arg Thr Ile Ala Arg Arg
                165                 170                 175

Ser His Gly Glu Val His Tyr Tyr Glu Ala Glu Ala Tyr Asp Val Asp
            180                 185                 190

Pro Glu Asn Lys Thr Ile Lys Val Lys Ser Ser Ala Lys Asn Asn Asp
        195                 200                 205

Tyr Asp Leu Asp Leu Lys Tyr Asp Tyr Leu Val Val Gly Val Gly Ala
    210                 215                 220
```

```
Gln Pro Asn Thr Phe Gly Thr Pro Gly Val Tyr Glu Tyr Ser Ser Phe
225                 230                 235                 240

Leu Lys Glu Ile Ser Asp Ala Gln Glu Ile Arg Leu Lys Ile Met Ser
            245                 250                 255

Ser Ile Glu Lys Ala Ala Ser Leu Ser Pro Lys Asp Pro Glu Arg Ala
        260                 265                 270

Arg Leu Leu Ser Phe Val Val Gly Gly Pro Thr Gly Val Glu
    275                 280                 285

Phe Ala Ala Glu Leu Arg Asp Tyr Val Asp Gln Asp Leu Arg Lys Trp
290                 295                 300

Met Pro Glu Leu Ser Lys Glu Ile Lys Val Thr Leu Val Glu Ala Leu
305                 310                 315                 320

Pro Asn Ile Leu Asn Met Phe Asp Lys Tyr Leu Val Asp Tyr Ala Gln
                325                 330                 335

Asp Leu Phe Lys Glu Glu Lys Ile Asp Leu Arg Leu Lys Thr Met Val
            340                 345                 350

Lys Lys Val Asp Ala Thr Thr Ile Thr Ala Lys Thr Gly Asp Gly Asp
        355                 360                 365

Ile Glu Asn Ile Pro Tyr Gly Val Leu Val Trp Ala Thr Gly Asn Ala
370                 375                 380

Pro Arg Glu Val Ser Lys Asn Leu Met Thr Lys Leu Glu Glu Gln Asp
385                 390                 395                 400

Ser Arg Arg Gly Leu Leu Ile Asp Asn Lys Leu Gln Leu Leu Gly Ala
                405                 410                 415

Lys Gly Ser Ile Phe Ala Ile Gly Asp Cys Thr Phe His Pro Gly Leu
            420                 425                 430

Phe Pro Thr Ala Gln Val Ala His Gln Glu Gly Glu Tyr Leu Ala Gln
        435                 440                 445

Tyr Phe Lys Lys Ala Tyr Lys Ile Asp Gln Leu Asn Trp Lys Met Thr
    450                 455                 460

His Ala Lys Asp Asp Ser Glu Val Ala Arg Leu Lys Asn Gln Ile Val
465                 470                 475                 480

Lys Thr Gln Ser Gln Ile Glu Asp Phe Lys Tyr Asn His Lys Gly Ala
                485                 490                 495

Leu Ala Tyr Ile Gly Ser Asp Lys Ala Ile Ala Asp Leu Ala Val Gly
            500                 505                 510

Glu Ala Lys Tyr Arg Leu Ala Gly Ser Phe Thr Phe Leu Phe Trp Lys
        515                 520                 525

Ser Ala Tyr Leu Ala Met Cys Leu Ser Phe Arg Asn Arg Val Leu Val
    530                 535                 540

Ala Met Asp Trp Ala Lys Val Tyr Phe Leu Gly Arg Asp Ser Ser Ile
545                 550                 555                 560

<210> SEQ ID NO 15
<211> LENGTH: 1683
<212> TYPE: DNA
<213> ORGANISM: Saccharomyces cerevisiae

<400> SEQUENCE: 15
atgattagac aatcattaat gaaaacagtg tgggctaact cctccaggtt tagcctacag      60
agcaagtcgg ggcttgtgaa atatgccaaa aatagatcgt tccatgcagc aagaaatttg     120
ctagaggaca agaaagtcat tttgcaaaaa gtgcgcccca ctactggcgt tgttgcgaag     180
cagtcctttt tcaagagaac tgggaaattt actttgaagg cttttattgta ttctgccctc     240
```

```
gcgggtacgg cttacgtttc atactcactt taccgagaag ctaacccttc tacccaagtt      300
cctcaatcgg acactttttcc aaacggttca agaggaaga ctttggtaat tctgggctcc      360
ggttggggtt ctgtgtcgct tttgaaaaat ttggacacca cgttgtataa tgttgttgtt      420
gtttctccaa gaattatttt tctttttact ccgctattgc catctacccc agttggtacc      480
atcgaattga atctattgt tgaacctgtc aggactattg ctagaagatc gcacggtgaa      540
gtccattact atgaagctga agcgtacgac gttgatcctg aaaacaaaac aattaaggtc      600
aaatcttccg ctaagaataa cgactacgac ttggacttga atacgacta tctggttgtc      660 ggtgtgggtg ctcaaccaaa cacttttggt actccgggag tttatgaata ttcttctttc      720
ttgaaggaaa tatccgacgc tcaagagatc agattaaaaa ttatgtccag tattgagaaa      780
gctgcctccc tatctccaaa agatcctgag agagcaagat tgttgagctt tgttgtcgtt      840
ggtggtggtc ccaccggtgt cgaatttgcc gctgaattga gagattatgt tgaccaggac      900
ttgagaaaat ggatgcccga attgagtaaa gaaattaaag tcactttggt ggaggctttg      960
ccaaacattt tgaacatgtt tgacaagtat ctcgttgact atgctcaaga tttattcaaa      1020
gaggaaaaaa tcgatttaag attgaaaaca atggttaaga agttgacgc taccactata      1080 actgccaaaa ctggcgatgg tgacattgaa aatataccgt atggtgtatt agtttgggct      1140
acaggtaatg cgccaagaga agtgtctaag aacctaatga ctaaattaga ggaacaggac      1200
tcaagacgtg gtttgttgat agataacaaa cttcaacttt tgggtgctaa gggatctatt      1260
tttgctatcg gcgattgtac cttccaccct ggcttgttcc ctaccgctca agttgcccac      1320
caagaaggtg aatacttggc tcagtatttc aagaaagctt ataaaatcga tcaattgaac      1380
tggaaaatga cccatgctaa agacgattca gaagtcgcta gattaaagaa ccaaatagtc      1440
aaaacgcaat cgcaaattga agacttcaag tacaaccata agggtgctct ggcttatatt      1500
ggttcagata aagccattgc tgatcttgcc gttggtgaag ccaaatatag gttagccggc      1560
tcattcacct tcctattctg gaaatctgct tatttggcaa tgtgtctatc ctttagaaac      1620
agagttcttg tcgctatgga ttgggctaaa gtttatttct tgggtagaga ttcatctatc      1680
tag                                                                    1683
```

<210> SEQ ID NO 16
<211> LENGTH: 545
<212> TYPE: PRT
<213> ORGANISM: Saccharomyces cerevisiae

<400> SEQUENCE: 16

Met Leu Pro Arg Leu Gly Phe Ala Arg Thr Ala Arg Ser Ile His Arg
1               5                   10                  15

Phe Lys Met Thr Gln Ile Ser Lys Pro Phe Phe His Ser Thr Glu Val
                20                  25                  30

Gly Lys Pro Gly Pro Gln Gln Lys Leu Ser Lys Ser Tyr Thr Ala Val
            35                  40                  45

Phe Lys Lys Trp Phe Val Arg Gly Leu Lys Leu Thr Phe Tyr Thr Thr
        50                  55                  60

Leu Ala Gly Thr Leu Tyr Val Ser Tyr Glu Leu Tyr Lys Glu Ser Asn
65                  70                  75                  80

Pro Pro Lys Gln Val Pro Gln Ser Thr Ala Phe Ala Asn Gly Leu Lys
                85                  90                  95

Lys Lys Glu Leu Val Ile Leu Gly Thr Gly Trp Gly Ala Ile Ser Leu
            100                 105                 110

```
Leu Lys Lys Leu Asp Thr Ser Leu Tyr Asn Val Thr Val Ser Pro
            115                 120                 125

Arg Ser Phe Phe Leu Phe Thr Pro Leu Pro Ser Thr Pro Val Gly
    130                 135                 140

Thr Ile Glu Met Lys Ser Ile Val Glu Pro Val Arg Ser Ile Ala Arg
145                 150                 155                 160

Arg Thr Pro Gly Glu Val His Tyr Ile Glu Ala Glu Leu Asp Val
                165                 170                 175

Asp Pro Lys Ala Lys Lys Val Met Val Gln Ser Val Ser Glu Asp Glu
                180                 185                 190

Tyr Phe Val Ser Ser Leu Ser Tyr Asp Tyr Leu Val Val Ser Val Gly
            195                 200                 205

Ala Lys Thr Thr Thr Phe Asn Ile Pro Gly Val Tyr Gly Asn Ala Asn
    210                 215                 220

Phe Leu Lys Glu Ile Glu Asp Ala Gln Asn Ile Arg Met Lys Leu Met
225                 230                 235                 240

Lys Thr Ile Glu Gln Ala Ser Ser Phe Pro Val Asn Asp Pro Glu Arg
                245                 250                 255

Lys Arg Leu Leu Thr Phe Val Val Val Gly Gly Pro Thr Gly Val
            260                 265                 270

Glu Phe Ala Ala Glu Leu Gln Asp Tyr Ile Asn Gln Asp Leu Arg Lys
                275                 280                 285

Trp Met Pro Asp Leu Ser Lys Glu Met Lys Val Ile Leu Ile Glu Ala
            290                 295                 300

Leu Pro Asn Ile Leu Asn Met Phe Asp Lys Thr Leu Ile Lys Tyr Ala
305                 310                 315                 320

Glu Asp Leu Phe Ala Arg Asp Glu Ile Asp Leu Gln Val Asn Thr Ala
                325                 330                 335

Val Lys Val Val Glu Pro Thr Tyr Ile Arg Thr Leu Gln Asn Gly Gln
            340                 345                 350

Thr Asn Thr Asp Ile Glu Tyr Gly Met Leu Val Trp Ala Thr Gly Asn
    355                 360                 365

Glu Pro Ile Asp Phe Ser Lys Thr Leu Met Ser Arg Ile Pro Glu Gln
    370                 375                 380

Thr Asn Arg Arg Gly Leu Leu Ile Asn Asp Lys Leu Glu Leu Leu Gly
385                 390                 395                 400

Ser Glu Asn Ser Ile Tyr Ala Ile Gly Asp Cys Thr Ala His Thr Gly
                405                 410                 415

Phe Phe Pro Thr Ala Gln Val Ala His Gln Glu Gly Leu Tyr Leu Ala
            420                 425                 430

Lys Ile Leu Asp Lys Lys Leu Gln Ile Glu Gln Leu Glu Trp Asp Met
    435                 440                 445

Leu Asn Ser Thr Asp Glu Thr Glu Val Ser Arg Leu Gln Lys Glu Val
450                 455                 460

Asn Leu Arg Lys Ser Lys Leu Asp Lys Phe Asn Tyr Lys His Met Gly
465                 470                 475                 480

Ala Leu Ala Tyr Ile Gly Ser Glu Thr Ala Ile Ala Asp Leu His Met
                485                 490                 495

Gly Asp Ser Ser Tyr Gln Leu Lys Gly Met Phe Ala Phe Leu Phe Trp
            500                 505                 510

Lys Ser Ala Tyr Leu Ala Met Cys Leu Ser Ile Arg Asn Arg Ile Leu
    515                 520                 525

Ile Ala Met Asp Trp Thr Lys Val Tyr Phe Leu Gly Arg Asp Ser Ser
```

Val
545

<210> SEQ ID NO 17
<211> LENGTH: 1638
<212> TYPE: DNA
<213> ORGANISM: Saccharomyces cerevisiae

<400> SEQUENCE: 17

| | | | | | |
|---|---|---|---|---|---|
| atgctgccca | gacttggttt | tgcgaggact | gctaggtcca | tacaccgttt | caagatgacc | 60 |
| cagatctcta | aacctttttt | ccattccact | gaagttggta | agcccggacc | acagcagaag | 120 |
| ctatcgaaat | cttacactgc | ggtattcaag | aaatggtttg | tcagaggttt | aaagttaacc | 180 |
| ttttacacga | cgttggccgg | cacattgtat | gtgtcatacg | agctgtacaa | agaatcgaac | 240 |
| ccacccaaac | aggttcccca | atcgaccgct | tttgctaatg | gtttgaaaaa | gaaggagctg | 300 |
| gttattttgg | gtacaggctg | gggcgccata | tctcttttga | agaaattaga | cacgtctttg | 360 |
| tataacgtga | ccgtggtgtc | gccaagaagc | ttcttttgt | tcacaccgtt | attccctca | 420 |
| acgcctgtgg | gtacgataga | gatgaagtct | attgtcgaac | cggttagatc | gatcgctaga | 480 |
| agaacgcctg | gagaagttca | ctacattgag | gcggaagcgt | tggacgttga | tccaaaggcc | 540 |
| aaaaaagtaa | tggtgcaatc | ggtgtcagag | gacgaatatt | tcgtttcgag | cttaagttac | 600 |
| gattatcttg | ttgttagtgt | aggcgctaaa | accactactt | ttaacattcc | cggggtctat | 660 |
| ggcaatgcta | acttcttgaa | agagattgaa | gatgctcaaa | atattcgtat | gaagttaatg | 720 |
| aaaaccatag | aacaggcaag | ttcatttcct | gtgaacgatc | cggaaaggaa | gcgattatta | 780 |
| acgttcgtgg | ttgttggagg | gggccctacg | ggggttgaat | ttgccgccga | actgcaagat | 840 |
| tacatcaatc | aagatttgag | gaagtggatg | cccgacttaa | gtaaagaaat | gaaggttatc | 900 |
| ttaattgaag | ccctgcctaa | tatcctaaac | atgttcgata | agacgttgat | caagtatgcc | 960 |
| gaggaccttt | ttgccagaga | tgaaattgac | ttgcaagtga | atactgccgt | gaaagtcgta | 1020 |
| gagccaacct | atatacgcac | tctgcaaaac | ggccaaacaa | acacggatat | cgaatacggg | 1080 |
| atgctggttt | gggccacggg | aaatgaacca | atcgattttt | caaagacact | gatgagtaga | 1140 |
| ataccggagc | aaactaatag | gcgtggtctg | ttaattaatg | acaagttgga | gcttctcggt | 1200 |
| tctgagaatt | cgatttatgc | aattggtgat | tgtaccgcac | acacgggttt | ctttcccacg | 1260 |
| gcacaagttg | cacatcagga | aggcgaatac | ttggccaaga | tcttggataa | aaaattacag | 1320 |
| atagaacaat | tggaatggga | catgctcaac | agtaccgatg | aaactgaggt | atcacgtcta | 1380 |
| caaaaagagg | ttaatttgag | gaaatctaag | ttggataagt | tcaactacaa | gcatatgggt | 1440 |
| gcccttgcgt | acatcggctc | tgaaaccgca | attgcagatt | tgcatatggg | cgactcatca | 1500 |
| taccagttga | aaggtatgtt | tgccttcttg | ttttggaaat | ccgcttattt | ggccatgtgt | 1560 |
| ctctctatca | ggaataggat | tttaattgcc | atggactgga | ccaaagttta | ctttcttgga | 1620 |
| agggattcct | ccgtgtag | | | | | 1638 |

<210> SEQ ID NO 18
<211> LENGTH: 1267
<212> TYPE: DNA
<213> ORGANISM: Artificial Sequence
<220> FEATURE:
<223> OTHER INFORMATION: Synthetic ARS/CEN

<400> SEQUENCE: 18

```
gagctccttt catttctgat aaaagtaaga ttactccatt tatcttttca ccaacatatt      60
catagttgaa agttatcctt ctaagtacgt atacaatatt aattaaacgt aaaaacaaaa     120
ctgactgtaa aaatgtgtaa aaaaaaaata tcaaattcat agcagtttca aggaatgaaa     180
actattatga tctggtcacg tgtatataaa ttattaattt taaacccata taatttatta     240 ttttttatt ctaaagttta aagtaatttt agtagtattt tatattttga ataaatatac      300
tttaaatttt tatttttata ttttattact tttaaaaata atgttttat ttaaaacaaa      360 attataagtt aaaaagttgt tccgaaagta aaatatattt tatagttttt acaaaaataa     420
attattttta acgtattttt tttaattata tttttgtatg tgattatatc cacaggtatt     480
atgctgaatt tagctgtttc agtttaccag tgtgatagta tgattttttt tgcctctcaa     540
aagctatttt tttagaagct tcgtcttaga aataggtggt gtataaattg cggttgactt     600
ttaactatat atcattttcg atttatttat tacatagaga ggtgcttta attttttaat      660 ttttattttc aataattta aaagtgggta cttttaaatt ggaacaaagt gaaaaatatc      720
tgttatacgt gcaactgaat tttactgacc ttaaaggact atctcaatcc tggttcagaa     780
atccttgaaa tgattgatat gttggtggat tttctctgat tttcaaacaa gaggtatttt     840
atttcatatt tattatattt tttacattta ttttatattt ttttattgtt tggaagggaa     900
agcgacaatc aaattcaaaa tatattaatt aaactgtaat acttaataag agacaaataa     960
cagccaagaa tcaaatactg ggttttaat caaagatct ctctacatgc acccaaattc      1020
attatttaaa tttactatac tacagacaga atatcgaac ccagattaag tagtcagacg     1080
cttttccgct ttattgagta tatagcctta catattttct gcccataatt tctggattta     1140
aaataaacaa aaatggttac tttgtagtta tgaaaaaagg ctttttccaaa atgcgaaata     1200 cgtgttattt aaggttaatc aacaaaacgc atatccatat gggtagttgg acaaaacttc     1260
aatcgat                                                                1267
```

<210> SEQ ID NO 19
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 19

```
atttggcgag cgttggttgg tggatcaagc ccacgcgtag gcaatcctcg agcagatccg      60
ccaggcgtgt atatatagcg tggatggcca ggcaacttta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289
```

<210> SEQ ID NO 20
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 20

```
atagcttcaa aatgtttcta ctccttttt actcttccag attttctcgg actccgcgca      60
tcgccgtacc acttcaaaac acccaagcac agcatactaa atttcccctc tttcttcctc     120
tagggtgtcg ttaattaccc gtactaaagg tttggaaaag aaaaaagaga ccgcctcgtt     180
```

```
tctttttctt cgtcgaaaaa ggcaataaaa attttatca cgtttctttt tcttgaaaat    240
tttttttttg atttttttct ctttcgatga cctcccattg atatttaagt taataaacgg    300
tcttcaattt ctcaagtttc agtttcattt ttcttgttct attacaactt tttttacttc    360
ttgctcatta gaaagaaagc atagcaatct aatctaagtt t                        401

<210> SEQ ID NO 21
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 21
agtttatcat tatcaatact cgccatttca agaatacgt aaataattaa tagtagtgat     60
tttcctaact ttatttagtc aaaaaattag cctttaatt ctgctgtaac ccgtacatgc    120
ccaaaatagg gggcgggtta cacagaatat ataacatcgt aggtgtctgg gtgaacagtt   180
tattcctggc atccactaaa tataatggag cccgcttttt aagctggcat ccagaaaaaa   240
aaagaatccc agcaccaaaa tattgttttc ttcaccaacc atcagttcat aggtccattc   300
tcttagcgca actacagaga acaggggcac aaacaggcaa aaacgggca caacctcaat    360 ggagtgatgc aacctgcctg gagtaaatga tgacacaagg caattgaccc acgcatgtat   420
ctatctcatt ttcttacacc ttctattacc ttctgctctc tctgatttgg aaaaagctga   480 aaaaaaggt tgaaaccagt tccctgaaat tattccccta cttgactaat aagtatataa    540
agacggtagg tattgattgt aattctgtaa atctatttct taaacttctt aaattctact   600
tttatagtta gtcttttttt tagttttaaa acaccagaac ttagtttcga cggat        655

<210> SEQ ID NO 22
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 22
ttcgcggcca cctacgccgc tatctttgca acaactatct gcgataactc agcaaatttt    60
gcatattcgt gttgcagtat tgcgataatg ggagtcttac ttccaacata acggcagaaa   120
gaaatgtgag aaaattttgc atcctttgcc tccgttcaag tatataaagt cggcatgctt   180
gataatcttt ctttccatcc tacattgttc taattattct tattctcctt tattctttcc   240
taacatacca agaaattaat cttctgtcat tcgcttaaac actatatcaa ta           292

<210> SEQ ID NO 23
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 23
gccgggatcg aagaaatgat ggtaaatgaa ataggaaatc aaggagcatg aaggcaaaag    60
acaaatataa gggtcgaacg aaaaataaag tgaaagtgt tgatatgatg tatttggctt    120
tgcggcgccg aaaaaacgag tttacgcaat tgcacaatca tgctgactct gtggcggacc   180
cgcgctcttg ccggcccggc gataacgctg ggcgtgaggc tgtgcccggc ggagtttttt   240
```

```
gcgcctgcat tttccaaggt ttaccctgcg ctaaggggcg agattggaga agcaataaga    300
atgccggttg gggttgcgat gatgacgacc acgacaactg gtgtcattat ttaagttgcc    360
gaaagaacct gagtgcattt gcaacatgag tatactagaa gaatgagcca agacttgcga    420
gacgcgagtt tgccggtggt gcgaacaata gagcgaccat gaccttgaag gtgagacgcg    480
cataaccgct agagtacttt gaagaggaaa cagcaatagg gttgctacca gtataaatag    540
acaggtacat acaacactgg aaatggttgt ctgtttgagt acgctttcaa ttcatttggg    600
tgtgcacttt attatgttac aatatggaag ggaactttac acttctccta tgcacatata    660
ttaattaaag tccaatgcta gtagagaagg ggggtaacac ccctccgcgc tcttttccga    720 ttttttttcta aaccgtggaa tatttcggat atccttttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actacccttt   1020
ttccatttgc catctattga agtaataata ggcgcatgca acttcttttc tttttttttc   1080
ttttctctct cccccgttgt tgtctcacca tatccgcaat gacaaaaaaa tgatggaaga   1140
cactaaagga aaaattaac gacaaagaca gcaccaacag atgtcgttgt tccagagctg   1200 atgagggta tctcgaagca cacgaaactt tttccttcct tcattcacgc acactactct   1260
ctaatgagca acggtatacg gccttccttc cagttacttg aatttgaaat aaaaaaaagt   1320
ttgctgtctt gctatcaagt ataaatagac ctgcaattat taatcttttg tttcctcgtc   1380
attgttctcg ttcccttct tccttgtttc tttttctgca caatatttca agctatacca   1440
agcatacaat caactccaag ctggccgc                                        1468

<210> SEQ ID NO 24
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 24
tcatgtaatt agttatgtca cgcttacatt cacgccctcc ccccacatcc gctctaaccg     60
aaaaggaagg agttagacaa cctgaagtct aggtccctat ttatttttt atagttatgt    120 tagtattaag aacgttattt atatttcaaa ttttctttt ttttctgtac agacgcgtgt    180
acgcatgtaa cattatactg aaaaccttgc ttgagaaggt tttgggacgc tcgaaggctt    240
taatttgcgg cc                                                         252

<210> SEQ ID NO 25
<211> LENGTH: 31
<212> TYPE: DNA
<213> ORGANISM: Artificial Sequence
<220> FEATURE:
<223> OTHER INFORMATION: Synthetic forward primer

<400> SEQUENCE: 25
cgagctcttc gcggccacct acgccgctat c                                    31

<210> SEQ ID NO 26
<211> LENGTH: 32
<212> TYPE: DNA
<213> ORGANISM: Artificial Sequence
```

<220> FEATURE:
<223> OTHER INFORMATION: Synthetic reverse primer

<400> SEQUENCE: 26
gctctagata ttgatatagt gtttaagcga at                          32

<210> SEQ ID NO 27
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 27
ggatccatgt ccgtaaagga actact                                 26

<210> SEQ ID NO 28
<211> LENGTH: 34
<212> TYPE: DNA
<213> ORGANISM: Artificial Sequence
<220> FEATURE:
<223> OTHER INFORMATION: Synthetic reverse primer

<400> SEQUENCE: 28
acgcgtcgac ttaaaactgc aattcctttt gaat                        34

<210> SEQ ID NO 29
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 29
gagctcaatt aaccctcact aaaggg                                 26

<210> SEQ ID NO 30
<211> LENGTH: 26
<212> TYPE: DNA
<213> ORGANISM: Artificial Sequence
<220> FEATURE:
<223> OTHER INFORMATION: Synthetic reverse primer

<400> SEQUENCE: 30
gagctccaaa ttaaagcctt cgagcg                                 26

<210> SEQ ID NO 31
<211> LENGTH: 69
<212> TYPE: DNA
<213> ORGANISM: Artificial Sequence
<220> FEATURE:
<223> OTHER INFORMATION: Synthetic forward primer

<400> SEQUENCE: 31
tgagcacgtg agtatacgtg attaagcaca caaaggcagc ttggagtatg gtgctgcaag    60
gcgattaag                                                           69

<210> SEQ ID NO 32
<211> LENGTH: 67
<212> TYPE: DNA
<213> ORGANISM: Artificial Sequence
<220> FEATURE:
<223> OTHER INFORMATION: Synthetic reverse primer

<400> SEQUENCE: 32
aggcaagtgc acaaacaata cttaaataaa tactactcag taataacccg gctcgtatgt    60
tgtgtgg                                                              67

<210> SEQ ID NO 33
<211> LENGTH: 21
<212> TYPE: DNA
<213> ORGANISM: Artificial Sequence
<220> FEATURE:
<223> OTHER INFORMATION: Synthetic forward primer

<400> SEQUENCE: 33
gccaaatgat ttagcattat c                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic reverse primer

<400> SEQUENCE: 34
aaaaggagag ggccaagagg g                                              21

<210> SEQ ID NO 35
<211> LENGTH: 60
<212> TYPE: DNA
<213> ORGANISM: Artificial Sequence
<220> FEATURE:
<223> OTHER INFORMATION: Synthetic forward primer

<400> SEQUENCE: 35
atgattagac aatcattaat gaaaacagtg tgggctaact ccagtcacga cgttgtaaaa    60

<210> SEQ ID NO 36
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 36
ctagatagat gaatctctac ccaagaaata aactttagcc aggtttcccg actggaaagc    60

<210> SEQ ID NO 37
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 37
actgatcatc atttaaaaat gt                                             22

<210> SEQ ID NO 38
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 38
aaggaaaaaa attttcacac ta                                             22

<210> SEQ ID NO 39
<211> LENGTH: 70

<212> TYPE: DNA
<213> ORGANISM: Artificial Sequence
<220> FEATURE:
<223> OTHER INFORMATION: Synthetic forward primer

<400> SEQUENCE: 39
atgctgccca gacttggttt tgcgaggact gctaggtcca tacaccgttt ccagtcacga    60
cgttgtaaaa    70

<210> SEQ ID NO 40
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 40
ctacacggag gaatcccttc caagaaagta aactttggtc aggtttcccg actggaaagc    60

<210> SEQ ID NO 41
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 41
caggaacata gtagaaagac    20

<210> SEQ ID NO 42
<211> LENGTH: 18
<212> TYPE: DNA
<213> ORGANISM: Artificial Sequence
<220> FEATURE:
<223> OTHER INFORMATION: Synthetic reverse primer

<400> SEQUENCE: 42
taacgcgaat cttccatg    18

<210> SEQ ID NO 43
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 43
atgagtaatc ctcaaaaagc tctaaacgac tttctgtcca gtgaatctgt ccagtcacga    60
cgttgtaaaa    70

<210> SEQ ID NO 44
<211> LENGTH: 70
<212> TYPE: DNA
<213> ORGANISM: Artificial Sequence
<220> FEATURE:
<223> OTHER INFORMATION: Synthetic reverse primer

<400> SEQUENCE: 44
tcatgttacc ttcttagcat taccataatg cgaatcttct gatgatgtgt aggtttcccg    60
actggaaagc    70

<210> SEQ ID NO 45
<211> LENGTH: 20
<212> TYPE: DNA

```
<213> ORGANISM: Artificial Sequence
<220> FEATURE:
<223> OTHER INFORMATION: Synthetic forward primer

<400> SEQUENCE: 45
atgagtaatc ctcaaaaagc                                               20

<210> SEQ ID NO 46
<211> LENGTH: 17
<212> TYPE: DNA
<213> ORGANISM: Artificial Sequence
<220> FEATURE:
<223> OTHER INFORMATION: Synthetic reverse primer

<400> SEQUENCE: 46
tcatgttacc ttcttag                                                  17
```